(12) United States Patent
Iversen et al.

(10) Patent No.: US 6,309,550 B1
(45) Date of Patent: Oct. 30, 2001

(54) MASS TRANSFER METHOD AND APPARATUS

(75) Inventors: Steen Brummerstedt Iversen, Copenhagen; Vinay Kumar Bhatia, Fredensborg; Kim Dam-Johansen, Frederiksværk; Gunnar Jonsson, Værløse, all of (DK)

(73) Assignee: FLS Miljo A/S, Valby (DK)

( * ) Notice: Subject to any disclaimer, the term of this patent is extended or adjusted under 35 U.S.C. 154(b) by 0 days.

(21) Appl. No.: 08/750,775

(22) PCT Filed: Jun. 22, 1995

(86) PCT No.: PCT/DK95/00263

§ 371 Date: Jan. 22, 1997

§ 102(e) Date: Jan. 22, 1997

(87) PCT Pub. No.: WO95/35153

PCT Pub. Date: Dec. 28, 1995

(30) Foreign Application Priority Data

Jun. 22, 1994 (DK) ................................................ 0746/94

(51) Int. Cl.[7] .......................... B01D 61/44; B01D 61/36
(52) U.S. Cl. ........................ 210/644; 210/640; 210/649; 95/43
(58) Field of Search ............................. 210/640, 500.36, 210/500.42, 500.41, 649, 644; 95/43, 45; 96/6

(56) References Cited

U.S. PATENT DOCUMENTS 3,339,341 9/1967 Maxwell et al. .
3,422,008 1/1969 McLain .

(List continued on next page.)

FOREIGN PATENT DOCUMENTS 435 693 11/1967 (CH) .
0 351 584 6/1989 (EP) .

(List continued on next page.)

OTHER PUBLICATIONS

Acda et al., "Behavioral Analysis of Air Perstripping", Journal of Membrane Science, vol. 67, No. 1, (1992) pp. 1–14.

(List continued on next page.)

*Primary Examiner*—Ana Fortuna

(57) ABSTRACT

The invention relates to a method for transferring mass between a flow of a first fluid, preferably a gas phase such as a combustion flue gas, and flow of a second fluid, preferably a liquid phase, where the first fluid is contacted with the outer surface of porous (semi-permeable) membranes, e.g. Polytetrafluoroethylene (PTFE, Teflon®) membranes, in the form of hollow fibers having gas-containing pores and containing the second fluid with the inner surface of the membranes. Useful membranes are characterized in that they e.g. have a porosity ($\epsilon$) of at least 0.50, a mass transfer coefficient of e.g. at least 3 cm/s, and a tortuosity factor of e.g. at the most $1.4/\epsilon$ when the porosity $\epsilon$ is lower than 0.80 and at the most $1.3/\epsilon$ when the porosity $\epsilon$ is 0.80 or higher. The membranes may also be arranged in hollow tubular members where the mass transfer coefficient of the membranes is at least on tenth of the mass transfer coefficient of the gas phase. The invention also relates to an apparatus for the above-mentioned mass transfer having a tubular conduit with an open inlet end, where a part of the wall of the conduit comprises a plurality of hollow tubular members defining array(s) with interstices between the members allowing flow of the gas phase. The invention further relates to a process for absorption or desorption where porous membranes, e.g. the above-characterized membranes, are utilized and where an exceptionally low membrane area per cubic meter of gas handled is required.

15 Claims, 16 Drawing Sheets

U.S. PATENT DOCUMENTS

| | | |
|---|---|---|
| 3,442,389 | 5/1969 | Mendelson . |
| 3,455,460 | 7/1969 | Mahon et al. . |
| 3,690,465 | 9/1972 | McGinnis et al. . |
| 3,899,309 | 8/1975 | Hoehn et al. . |
| 3,953,566 | 4/1976 | Gore . |
| 4,207,192 | 6/1980 | Coplan et al. . |
| 4,293,418 | 10/1981 | Fujii et al. . |
| 4,369,605 | 1/1983 | Opersteny et al. . |
| 4,430,219 | 2/1984 | Kuzumoto et al. . |
| 4,690,873 | 9/1987 | Makino et al. . |
| 4,717,394 | 1/1988 | Hayes . |
| 4,758,341 | 7/1988 | Banner . |
| 4,781,834 | 11/1988 | Sekino et al. . |
| 4,790,857 * | 12/1988 | Miksch ................................... 95/45 |
| 4,911,846 | 3/1990 | Akasu et al. . |
| 4,961,760 | 10/1990 | Caskey et al. . |
| 5,026,479 * | 6/1991 | Bickson et al. ................... 210/321.8 |
| 5,167,824 | 12/1992 | Cohen et al. . |
| 5,169,530 | 12/1992 | Schucker et al. . |
| 5,232,600 * | 8/1993 | Degen et al. ......................... 210/640 |
| 5,264,171 | 11/1993 | Prasad et al. . |
| 5,382,364 * | 1/1995 | Bowser et al. ....................... 210/640 |
| 5,582,735 * | 12/1996 | Mancusi, III et al. .............. 210/640 |
| 5,637,224 * | 6/1997 | Sirkar et al. ......................... 210/644 |
| 5,639,375 * | 6/1997 | Hiroshi ................................. 210/640 |
| 5,723,769 * | 3/1998 | Barber et al. ......................... 210/640 |

FOREIGN PATENT DOCUMENTS

| | | |
|---|---|---|
| 0 374 873 | 6/1990 | (EP) . |
| 0 466 947 | 9/1991 | (EP) . |
| 0 470 377 | 2/1992 | (EP) . |
| 0 562 520 | 9/1993 | (EP) . |
| 2 025 256 | 1/1980 | (GB) . |

OTHER PUBLICATIONS

Schofield et al., "Gas and Vapour Transport Through Microporous Membranes", Journal of Membrane Science, vol. 53, No. 1/2, (1990) pp. 173–185.

Fujii et al., "Slectivity and Characteristics of Direct Contact Membrane Distillation Type . . . ", Journal of Membrane Science, vol. 72, No. 1, (1992) pp. 53–72.

Michaels et al., "Flow of Gases Through Polyethylene", Journal of Polymer Science, vol. L, (1961) pp. 413–439.

"Hollow–Fiber Membranes", Hollow–Fiber Membranes, vol. 12, pp. 492–517.

Kesting, "Synthetic Polymeric Membranes", McGraw–Hill, (1971) pp. 29–40.

Mulder, "Basic Principles of Membrane Technology", Kluwer Academic Publishers, pp. 112–133.

Wang et al., "Baffled Membrane Modules Made With Hollow Fiber Fabric", Journal of Membrane Science, vol. 85, (1993) pp. 265–278.

Wickramasinghe et al., "Better Hollow Fiber Contractors", Journal of Medicine Science, vol. 62, (1991) pp. 371–388.

Carberry, J.J. & Warma, A., "Chemical reaction and reactor engineering" pp. 239–292, marcel Dekker Inc., New York, 1987.

Mason, E.A. & Malinaukas, A.P., "Gas transport porous media: The dusty gas model" pp. 11–72, Elsevier Science Publ., B.V., 1983.

* cited by examiner

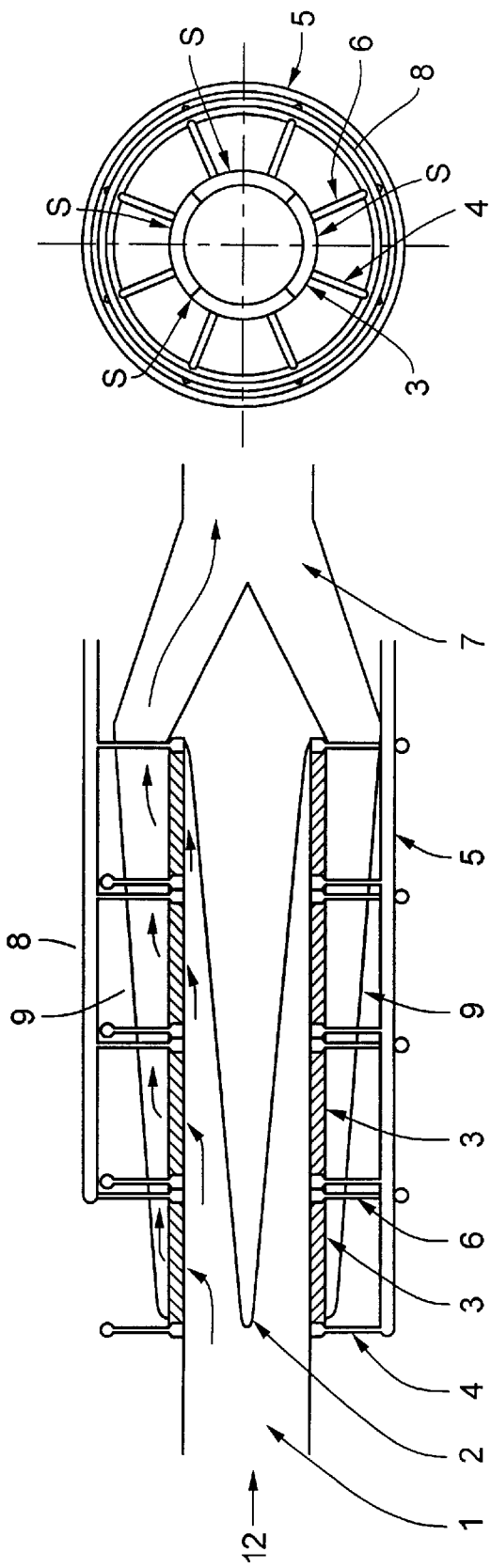

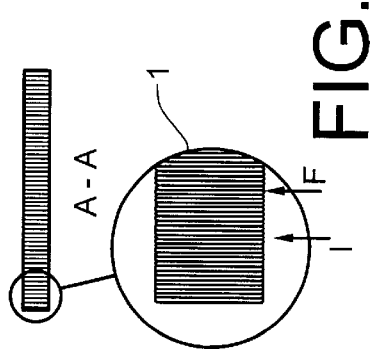
FIG. 14
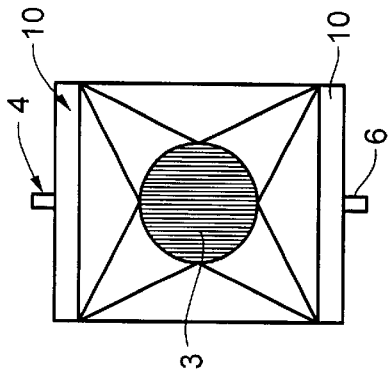
FIG. 16
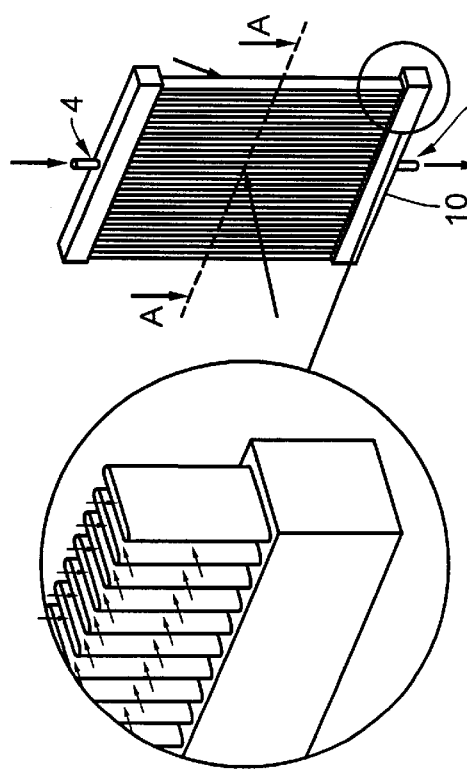
FIG. 13A
FIG. 13B
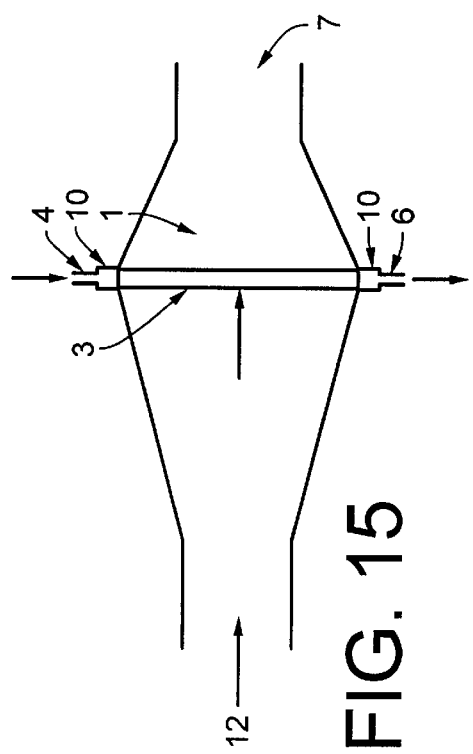
FIG. 15

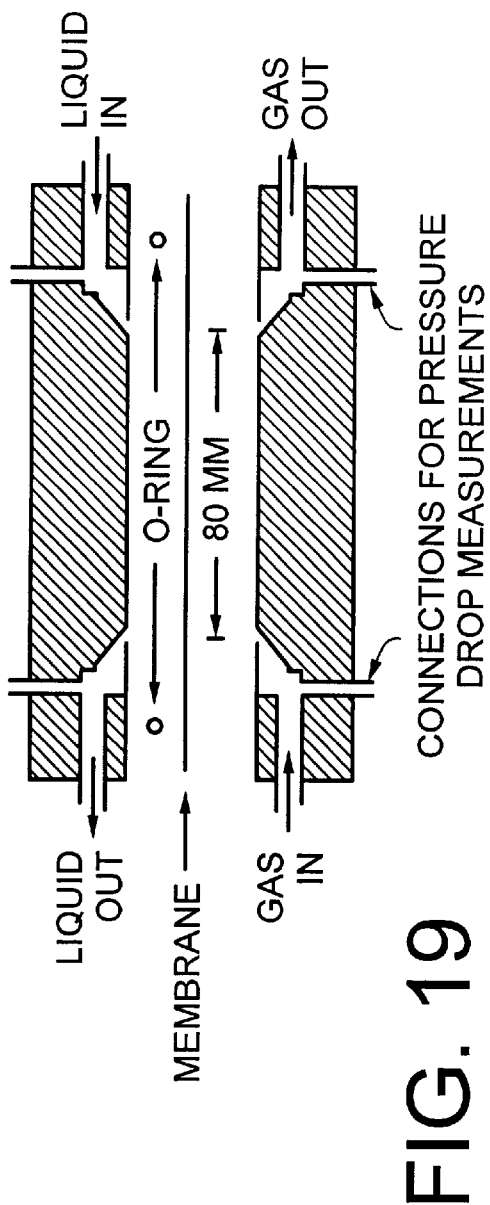
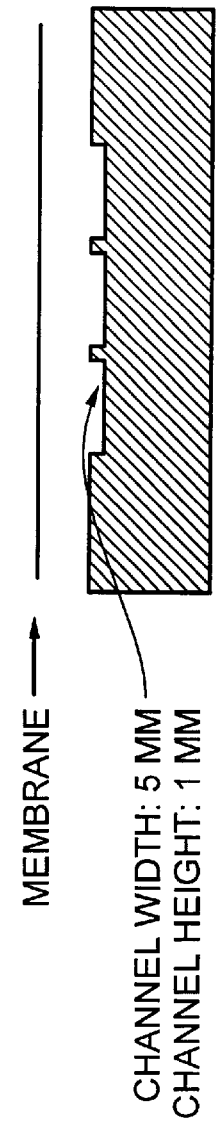

MASS TRANSFER METHOD AND APPARATUS

The present invention relates to a method for achieving mass transfer, i.e. transfer of one or more substances, from a flow of a first fluid to a flow of a second fluid, at least one of the fluids being a gas phase (where the term gas includes vapour), the other fluid being a liquid phase. More specifically, the invention relates to a method for mass transfer between such first and second fluids, comprising contacting the first fluid with the outer surface of one or more hollow tubular member(s) at least a part of which comprising one or more porous membrane(s) and contacting the second fluid with the inner surface of the hollow tubular member(s).

The invention also relates to an apparatus suitable for achieving mass transfer from a first fluid to a second fluid.

BACKGROUND

A hollow fibre membrane is a capillary whose wall functions as a semipermeable membrane. Hollow fibre membranes cover a wide range of separation problems with a specific membrane, of suitable membrane characteristics, being most suitable for each problem. The membrane characteristics need to be established to ascertain the optimal membrane for specific application. Such characterisation methods may be different depending upon the mechanism of specific separation, as will become clear from the description provided below.

The membranes for use in achieving mass transfer from a first fluid to a second fluid are unusual in membrane processes, in that the membranes are essentially nonselective. The selectivity for the species transferred is achieved by careful selection of the first fluid and the second fluid. Moreover, transport (mass transfer) of a species or component across the membrane are generally diffusion driven by an imposed concentration gradient (partial pressure gradient) of the component between the inside and the outside of the hollow fibre, and/or diffusion driven by chemical absorption.

The production of hollow fibres, used for conventional membrane processes such as reverse osmosis, ultrafiltration, microfiltration, dialysis, gas separation, pervaporation etc., are well known in the prior art (e.g. U.S. Pat. Nos. 3,899,309, 4,293,418, 4,430,219, 4,690,873, 4,717,394, 4,758,341, 4,781,834, 4,911,846, 4,961,760, 5,026,479, EP-A 0446947, Cabasso, I. et al. "Hollow Fibre membranes", Kirk-Othmer: Encycl. of Chem. Tech., Vol 12, 3. ed., pp 492–517 (1980)).

In the production of hollow fibre membranes, the critical physical parameters are generally considered to be the diameter of the hollow fibre, the wall thickness, the pore size, and the porosity of the membrane.

The basic wall morphology of the hollow fibres has been selected to obtain desired hydraulic permeability and desired mechanical properties. The key concerns for membrane characteristics for pressure driven processes such as reverse osmosis, ultrafiltration, microfiltration, gas separation etc. have been hydraulic permeability (i.e. convective permeability) and rejection characteristics of the membranes. Characterization of suitable hollow fibre membranes for such applications is well described in the prior art (e.g. Kesting, R. E., "Synthetic Polymeric membranes", McGraw-Hill Book Company, 1971; Mulder, M., "Basic principles of membrane technology", Kluwer Academic Publ., Dordrect, 1991). Generally, structural parameters as thickness, pore size and porosity of the membrane are combined in a hydraulic permeability constant, which is measured directly by a suitable method. Such measurement of hydraulic permeability, when used in combination with retention characteristics, such as the molecule cut off value, specifies the transport characteristics of the membrane.

When dealing with mass transfer through hollow fiber membranes with gas-containing pores, the same concerns have guided the selection of suitable membranes. Thus, e.g., EP 0374873 discloses the use of hollow fibre membranes for absorption/desorption where the hydraulic permeability has been specified for selecting the membrane.

BRIEF DESCRIPTION OF THE INVENTION

According to the present invention, it has been found that the above-mentioned parameter set is not the most relevant parameter set with respect to characterizing the suitability of a membrane for achieving mass transfer between two fluid flows; this is particularly true when dealing with high mass transfer rate diffusional transport between a gas and a liquid through a membrane with gas-containing pores where the controlling resistance is in the gas phase and/or the membrane. According to the invention, it has been found that membranes with gas-containing pores which show a surprisingly high mass transfer rate with respect to mass transfer between a gas and another fluid are membranes which have a low tortuosity factor and, in particular, membranes which come close to the tortuosity/porosity relation of $\tau=1/\epsilon$. As will appear from the detailed description herein, this discovery gives rise to a new understanding of the decisive criteria for designing hollow fibre membrane mass transfer processes and apparatus and thereby to new kinds of such processes and apparatus with much higher efficiencies than hitherto.

Thus, in one aspect, the invention relates to a method for transferring mass between a flow of a first fluid and a flow of a second fluid, at least one of the fluids being a gas phase, comprising contacting the first fluid with the outer surface of one or more porous membranes in the form of one or more hollow fibres the pores of which membranes are gas-containing and contacting the second fluid with the inner surface of said membranes, the maximum pore size of said membranes being such as to prevent direct mixing of the two fluids, the membranes having a porosity ($\epsilon$) of at least 0.50, the mass transfer coefficient of the membranes is at least 3 cm/s, and the tortuosity factor, as defined herein, of the membranes is at the most $1.4/\epsilon$ when the porosity $\epsilon$ is lower than 0.80 and at the most $1.3/\epsilon$ when the porosity $\epsilon$ is 0.80 or higher.

The mass transfer coefficient of the membranes with respect to the mass transfer in question is indicative of the capability of the membranes to transfer mass in the process in question; this mass transfer coefficient is explained and defined in detail below. The mass transfer film coefficient with respect to the mass transfer in question is indicative of the mass transfer which would take place between the two fluids in question; as will be understood, one of the fluids will have a lower mass transfer film coefficient than the other fluid and will thus be the limiting factor in the mass transfer. What is expressed above is that the membranes are so selected or adapted that where the membranes will not be the limiting factor (that is, where the mass transfer coefficient of the membrane is equal to or higher than the mass transfer film coefficient of the limiting fluid) or will be limiting only to a moderate extent, the preferred situation, now made possible and realistic through the present invention, being, of course, the situation where the membrane has little limiting effect or no limiting effect at all. As will appear from the following description of utilizations of the invention, this possibility of designing mass transfer processes and apparatus where the hollow fibre membranes have little or no limiting effect give rise to extremely efficient and fast mass transfer rate processes of types which would previously not have seemed economically realistic.

The key to the extremely high efficiencies obtainable using the principles of the present invention is the special tortuosity "rule" expressed by the tortuosity factor, τ, being close to 1/ε. The tortuosity factor of a porous material will be explained in detail in the following. The tortuosity factor depends on the geometric structure of the material and is dependent, inter alia, on the manufacturing process of the material. As will appear from the comparative examples which follow, selection of a hollow fibre membrane based on the tortuosity factor considerations above will result in the selection of other materials than would be selected using the prior art parameter set, and in the selection of far more efficient membrane materials than using the parameter set of the prior art.

As will be understood from the following theoretical explanation, the tortuosity factor is related to the porosity of a material, and this is the background for the criterion that the tortuosity factor should be at the most 1.3/ε when the porosity, ε, defined as the fraction of the free volume or pore volume of a material relative to the total volume of the material, determined by well-known physical measurements, such as $N_2$ adsorption/desorption, is 0.80 or higher.

It will be understood that hollow fibres can generally be considered as hollow tubular members. Thus, in the following, the term "hollow tubular members" comprises hollow fibres, and any other hollow tubular bodies having any cross-section, e.g, the hollow chamber described further below.

In a broader aspect, the invention relates to a method for transferring mass between a flow of a first fluid and a flow of a second fluid, one of the fluids being a gas phase and the other being a liquid phase, the method comprising contacting the first fluid with the outer surface of a plurality of hollow tubular members, at least part, but preferably substantially all, of the walls of the hollow tubular members comprising porous membranes with gas-containing pores and contacting the second fluid with the inner surface of said hollow tubular members, the maximum pore size of said membranes being such as to prevent direct mixing of the two fluids, the wall morphology of the membranes being so adapted that the mass transfer coefficient of the membranes with respect to the mass transfer in question is at least one tenth of the mass transfer coefficient of the gas phase, the hollow tubular members being arranged parallel to each other or at angles to each other, the plurality of hollow tubular members defining interstices therebetween through which interstices the first fluid is moved in a transverse direction relative to the longitudinal direction of the hollow tubular members.

In a still further aspect, the invention relates to an apparatus for transferring mass between a flow of a gas phase and a flow of a liquid phase, the apparatus comprising a tubular conduit having an open inlet end, at least a part of the wall of the tubular conduit comprising at least one gas-penetrable array of hollow tubular members, at least a part, but preferably substantially all, of the walls of the hollow tubular members comprising porous membranes having gas-containing pores, the maximum pore size of the membranes being such as to prevent direct mixing of the gas phase and the liquid phase, the plurality of hollow tubular members defining at least one array with interstices between the members allowing flow of the gas.

Due to a new understanding of the parameters relevant for mass transfer over a porous membrane which resulted in the present invention and of the importance of the suitable designs in which the membranes are utilized, the method for mass transfer may also be formulated in terms of the low membrane area required for a particular mass transfer operation.

Thus, in another aspect, the present invention relates to a process where a mass is transferred between a flow of a first fluid and a flow of a second fluid, one of the fluids being a gas phase and the other phase being a liquid phase, the first fluid being contacted with the outer surface of a plurality of porous membranes in the form of hollow fibres with gas-containing pores and the second fluid being contacted with the inner surface of said membranes, the maximum pore size of said membranes being such as to prevent direct mixing of the two fluids, the process being an absorption or a desorption process in which a component is removed from a gas or liquid phase, respectively, wherein, with reference to Equation 9 herein the membrane area required per cubic meter of gas phase handled per second, $A_m/G$, for $C_1/C_2$ equal to or greater than 20, $C_1$ being the inlet concentration, in the gas, of the component in question, and $C_2$ being the outlet concentration, in the gas, of the component in question, is at most 200 m$^2$/(m$^3$/s) where each C* is at most 0.05·C, or is at most 500 m$^2$/(m$^3$/s) where each C* is greater than 0.05·C.

Theoretical Section

For transport of a species across the membrane, the steady state flux of a species i through the gas-containing pores, as a result of a partial pressure difference, is characterized by the following relationship:

$$J_i = k_{i,1}(C_{i,1}^{bulk} - C_{i,1}^{mem}) = k_{i,m}(C_{i,1}^{mem} - C_{i,2}^{mem}) \quad (1)$$
$$= k_{i,2}(C_{i,2}^{mem} - C_{i,2}^{bulk}) = K_{i,o}(C_{i,1}^{bulk} - C_{i,2}^{bulk})$$

where J is the steady state flux across the membrane (measured in moles/(m$^2$·sec)), $C_{i,1}^{bulk}$ and $C_{i,2}^{bulk}$ are the bulk concentrations (e.g. in moles/m$^3$) of species i in the fluid phase 1 and 2, respectively, and $C_{i,1}^{mem}$ and $C_{i,2}^{mem}$ are the concentrations of species i (e.g. in moles/m$^3$) at the fluid phase 1/membrane boundary and membrane/fluid phase 2 boundary, respectively. The k values are the mass transfer coefficients in the individual phases (e.g. in m/s). $K_{i,o}$, is the overall mass transfer coefficient given by:

$$K_{i,o} = \frac{1}{\frac{1}{k_{i,1}} + \frac{1}{k_{i,m}} + \frac{1}{k_{i,2}}} \quad (2)$$

where $k_{i,1}$ and $k_{i,2}$ are the mass transfer coefficients for a species i in fluid phase 1 and 2, respectively, and $k_{i,m}$ is the intrinsic membrane mass transfer coefficient of species i.

Generally in the case for contacting processes, controlled by a liquid side resistance in conventional equipment (e.g. $O_2$ absorption into water or blood), the resistance to mass transfer in the liquid phase is so high that almost any known microporous membrane fulfilling the basic requirement to prevent direct mixing of the fluid phases, can be employed without significant contribution to the overall mass transfer rates.

However, many applications according to the method of the present invention involve contacting a gas phase with a liquid phase, where the liquid phase resistance is substantially negligible and the mass transfer is controlled by the resistance in the gas phase. For such high transfer rate applications, the mass transfer resistance in the membrane may limit the overall transfer rates, if the membrane wall morphology is not suitably controlled in the production process.

The transport of gas phase species i through the membrane is described by models for diffusion in porous media, available in the literature (e.g. Carberry, J. J. & Varma, A., "Chemical reaction and reactor engineering", Marcel Dekker Inc. New York, 1987; Mason, E. A. & Malinaukas, A. P., "Gas transport in porous media: The dusty gas model", Elsevier Science Publ. B. V., 1983). The intrinsic membrane mass transfer coefficient can be defined as in which t is the wall thickness of the hollow fibre (e.g. in m), $\epsilon$ is the membrane porosity expressed as the fraction of $$k_{i,m} = \frac{D_{i,comb}\epsilon}{t\tau} \quad (3)$$

total volume occupied by the pores (i.e. the fractional void space of the membrane), $\tau$ is a tortuosity factor, and $D_{i,comb}$ (e.g. in m$^2$/s) is a pseudo binary diffusion coefficient combined from the binary diffusion coefficient and the Knudsen diffusion coefficient by the Bozanquet interpolation equation $$\frac{1}{D_{i,comb}} = \frac{1}{D_i} + \frac{1}{D_{i,K}} \quad (4)$$

where $D_i$ (e.g. in m$^2$/s) is the binary diffusion coefficient for species i in the gas (taken from standard reference tables) and the Knudsen diffusion coefficient $D_{i,K}$ (e.g. in m$^2$/s). $D_{i,k}$ is obtained from the relation for long, straight, circular pores with diffuse scattering (Mason, 1983)

$$D_{i,K} = \frac{4}{3}r_p 10^{-4}\sqrt{\frac{2RT}{\pi M_i}} = 0.97 r_p \sqrt{\frac{T}{M_i}} \quad (5)$$

where $r_p$ is the average pore radius across the membrane (e.g. in m), R is the universal gas constant (e.g. in (kg·m$^2$)/(s$^2$·mole·K)), T is the absolute temperature (e.g. in K) and $M_i$ is the molecular weight of species i.

The pore size, $r_p$, to be used in equation 5 is the nominal (average) pore radius for diffusion across the membrane. The pore size will normally be provided by the membrane manufacturer, and may be measured by the well-known bubblepoint method, based on the Kelvin-Laplace equation (Kesting, 1971; Mulder, 1991 etc.). It should be understood that the nominal pore radius determined from retention measurements is not suitable, because it results in a minimum pore size and not the average pore size across the membrane.

For measuring the average pore size across the membrane, the membrane is placed in a membrane cell in contact with a liquid capable of wetting all the pores (e.g. methanol, isopropanol, etc.). The maximum pore size, the pore size distribution and average pore size for flow can then be determined by measuring the gas flux versus pressure characteristics for the dry membrane (dry flow curve), and for the wetted membrane (wet flow curve) as shown in FIG. 25.

Penetration of gas through the wetted membrane will first occur through the largest pores. The maximum pore size is determined at the pressure, where the first bubble pass the membrane as illustrated in FIG. 25. Similarly, the minimum pore size is determined, where the wet flow curve reach the dry flow curve. The average pore size as used herein is determined at the pressure, where the wet flow curve reach half of the dry flow curve.

The tortuosity factor, $\tau$, employed in the characterization of a porous membrane in the context of the invention is a value determined for the case where a standard gas mixture containing dilute $SO_2$ is supplied to the inside of the fibre in question and the other fluid is a 0.5 M sodium sulfite solution (with which $SO_2$ reacts to form $HSO_3^-$ ion in solution). Both fluid phases are at ambient temperature (T=293±5 K).

The relationships given by equation 1–5 above then apply with i=$SO_2$. Under these conditions the value of the liquid side resistance $1/k_{i,2}$ is negligible at sufficiently high sulfite loading of the liquid phase (sodium sulfite solution), so that equation (2) reduces to:

$$\frac{1}{K_{SO_2,o}} = \frac{1}{k_{SO_2,1}} + \frac{1}{k_{SO_2,m}} \quad (6)$$

The value of $k_{SO2,l}$ may be calculated using the well-known Graetz-Leveque solution for laminar flow within fibres (e.g. Wang, K. L. & Cussler, E. L., "Baffled membrane modules made with hollow fibre fabric", J. Memb. Sci., 85 (3), 265–279, 1993; Wickramasinghe, S. R., Semmens, M. J. and Cussler, E. L., "Better hollow fiber contactors", J.Memb. Sci., 62, 371–388, 1991):

$$k_{SO_2,1} = 1.62\left(\frac{D_{SO_2}}{d_{fibre}}\right)Gr^{0.33} = 1.62\left(\frac{D_{SO_2}}{d_{fibre}}\right)\left(\frac{d_{fibre}^2 V_{av}}{D_{SO_2} l}\right)^{0.33} \quad (7)$$

where $D_{SO2}$ is the binary diffusion coefficient for $SO_2$ in the gas, $d_{fibre}$ is the internal diameter of the hollow fibre in question, $V_{av}$ is the average gas flow velocity of gas within the hollow fibre [given by the gas flow rate (e.g. in m$^3$/s) divided by the cross sectional area [$\pi/4 \cdot (d_{fibre})^2$], and l is the effective length (excluding potting) of the hollow fibre membrane (e.g. in m).

The value of the overall mass transfer coefficient, $K_{SO2,o}$, is calculated from the relationship in formula 8:

$$K_{SO_2,o} = \frac{J_{SO_2}}{\left(\frac{C_{SO_2,1}^{bulk,in} - C_{SO_2,1}^{bulk,out}}{\ln\frac{C_{SO_2,1}^{bulk,in}}{C_{SO_2,1}^{bulk,out}}}\right)} = \frac{G}{\pi d_{fibre} l}\ln\left(\frac{C_{SO_2,1}^{bulk,in}}{C_{SO_2,1}^{bulk,out}}\right) \quad (8)$$

where J is the measured flux of $SO_2$ across the membrane, $(C_{SO2,l})^{bulk,in}$ is the concentration of $SO_2$ in the standard mixture supplied to the inside of the hollow fibre in question, and $(C_{SO2,l})^{bulk,out}$ is the measured concentration of $SO_2$ in the gas emerging from the hollow fibre. G is the gas flow rate of the standard gas supplied to the inside of the hollow fibre, $d_{fibre}$ the internal fibre diameter and l the effective length of the hollow fibre.

Having obtained the values for $K_{SO2,o}$ and $k_{SO2,l}$, the value of $k_{SO2,m}$ for the particular hollow fibre in question, may be calculated from equation (6) and the tortuosity factor, $\tau$, is then calculated from equation (3).

Thus, on the basis of the above, the membrane parameters employed in the context of the present invention may be measured or calculated for a given hollow fibre membrane.

DETAILED DESCRIPTION OF THE INVENTION

A hollow tubular member, and in particular a hollow fibre, employed in the context of the present invention may have one of a variety of cross sectional shapes, e.g. square, rectangular or substantially rectangular, elliptic (oval) or substantially elliptic, super elliptic or substantially super elliptic, or circular or substantially circular, polygonal or substantially polygonal, or the cross-section may be irregular in shape, etc. It is generally preferred that the hollow fibre is circular or substantially circular in cross section. Preferably the cross-sectional shape of the elongated chamber is oblong. The cross-section of the individual chambers is preferably substantially identical through the chamber array. For other cross sectional shapes than circular, $d_{fibre}$ is estimated by the hydraulic diameter.

In the present description with claims the term "surface of a membrane" and similar expressions are intended to mean at least a part of a membrane surface. Thus, e.g., in interesting embodiments of the present invention (see further below) the hollow fibre membranes arrays are "potted" in a potting material in order to allow the inner membrane surface to be sealed from the outer membrane surface. In this case it is iobvious that only a part of the outer membrane surface is accessible for the first fluid. The same principle also applies for the term "surface of a chamber" and similar expressions.

As mentioned above, one aspect of the invention relates to a method for transferring mass between a flow of a first fluid and a flow of a second fluid, at least one of the fluids being a gas phase, comprising contacting the first fluid with the outer surface of one or more porous membranes in the form of one or more hollow fibres the pores of which membranes are gas-containing and contacting the second fluid with the inner surface of said membranes, the maximum pore size of said membranes being such as to prevent direct mixing of the two fluids, the membranes having a porosity ($\epsilon$) of at least 0.50, the mass transfer coefficient of the membranes is at least 3 cm/s, and the tortuosity factor, as defined herein, of the membranes is at the most $1.4/\epsilon$ when the porosity $\epsilon$ is lower than 0.80 and at the most $1.3/\epsilon$ when the porosity $\epsilon$ is 0.80 or higher.

The hollow fibre will normally have an external diameter of at the most 3 mm, such as at the most 2 mm. An external diameter of at the most 1.5 mm, such as at the most 1 mm, will often be appropriate. For many applications according to the invention, an external diameter of at the most 0.8 mm will be preferred, and the ranges which are believed to be the most important are 0.2–0.8 mm, in particular 0.3–0.7 mm, such as 0.4–0.6 mm.

It will be understood that there should be a reasonable compromise between the requirement of sufficient mechanical strength and the requirement of efficient transport properties. On this basis, the ratio between the external diameter and the thickness of the fibre is normally in the range of 2–20 such as 5–15, preferably 10–15.

As regards to the wall thickness of the hollow fibre, it is believed that a thickness of at the most 300 $\mu$m will normally be appropriate for many applications of the method of the invention. Among these, fibres having a wall thickness of at the most 200 $\mu$m, such as fibres having a wall thickness in the range 5 to 200 $\mu$m, e.g. 10 to 200 $\mu$m, more particularly from 20 and 200 $\mu$m, such as between 20 and 150 $\mu$m, will normally be preferred. Especially preferred thicknesses are in the range between 20 and 100 $\mu$m, such as 20 and 80 $\mu$m, in particular between 20 and 60 $\mu$m.

As explained above, the porosity of the hollow fibre membrane is an important parameter (vide supra), and it is generally to be preferred that the porosity is at least 0.30. However, at porosity of at least 0.50, more preferably in the range of 0.50–0.90, such as 0.60–0.90, in particular 0.65–0.90, will generally lead to the best results. Subject, e.g., to the physical strength of the material of the hollow fibre, a porosity in the range of 0.70–0.90, such as 0.75–0.90, will often be a desirable range.

With respect to the tortuosity factor, as defined above, a value more closely approaching the theoretical limit of $1/\epsilon$ is to be preferred, such as a value of $1.3/\epsilon$, more preferably at the most $1.2/\epsilon$, and better still at the most $1.1/\epsilon$. A very desirable range is from $1/\epsilon$ to $1.1/\epsilon$.

The membrane mass transfer coefficient, given by Equation 3, is an important parameter for characterizing the mass transfer capability of the membrane. In the light of the discovery that a tortuosity as close as possible to $1/\epsilon$ gives superb properties opening new perspectives, the mass transfer capability for a given species of hollow fibres fulfilling this essential criterion can be considered to be predominantly and in most cases almost exclusively determined by the wall morphology factor ($\epsilon^2/t$). As appears from an analysis of various parameter combinations in Comparative Example 2, the ratio ($\epsilon^2/t$) should normally be at least 3 $mm^{-1}$, and, considering realistic mechanical strength limitations together with the desire of as high a morphology factor as possible, will preferably in the range of 3–100 $mm^{-1}$, such as in the range of 10–80 $mm^{-1}$, in particular in the range of 10–50 $mm^{-1}$.

It is preferred that the mass transfer coefficient is at least 1 cm/s, such as at least 2 cm/s, in particular at least 3 cm/s, such as 3–100 cm/s, and in particularly preferred embodiments of the invention, the mass transfer coefficient is 10–80 cm/s, such as 10–50 cm/s, in particular 10–30 cm/s.

The maximum pore size of the hollow fibre should generally be such as to prevent direct mixing of the two phases. However, the average pore radius across the membrane should not be too small, in order to minimize the influence of Knudsen diffusion. The broadest range of the average pore size which can be considered realistic is b 0.01$\mu$m to 3.00 $\mu$m, as determined by the bubblepoint method, but a smaller average pore size than 3.00 $\mu$m and a larger average pore size than 0.01 $\mu$m are greatly preferred, for which reason the average pore size is normally.in the range of 0.1 to 1.5 $\mu$m, more preferably in the range 0.2 $\mu$m to 1 $\mu$m or better still 0.3 $\mu$m to 0.8 $\mu$m. A very desirably range is from 0.4 $\mu$m to 0.6 $\mu$m, such as approximately 0.5 $\mu$m. Above this pore size the relative influence of Knudsen diffusion will be less than about 10%. The diameter ratio between the largest and the smallest pore size will normally be at the most 10, preferably at the most about 5, and more preferably at the most about 3.

From considerations concerning mass transfer performance of the fibre, the necessary liquid to gas ratios and considerations concerning wetting or fluid phase mixing, the ratio between the length of the fibre and the internal diameter of the fibre will normally be in the range of 1000–100000, preferably 2000–35000, and more preferably 5000–20000.

When combining the most interesting parameters in relevant parameter sets, the following most preferred combinations resulting in very interesting hollow membrane fibres are arrived at:

The external diameter of the fibre is in the range of 0.3–0.7 mm, in particular 0.4–0.6 mm, the ratio between the length of the fibre and the internal diameter of the fibre is 2000–35000, in particular 5000–20000, the membrane thickness is 20–50 μm, in particular about 30 μm, the pore size is in the range of 0.2–0.6 μm, the porosity is at least 0.70, in particular 0.75–0.90, and the tortuosity factor is $1/\epsilon$–$1.4/\epsilon$, in particular $1/\epsilon$–$1.3/\epsilon$, preferably $1/\epsilon$–$1.2/\epsilon$, and more preferably $1/\epsilon$–$1.1/\epsilon$.

As will be apparent from the disclosure above, in order that a hollow fibre for use in the present context can conform to the stated requirements, some limitations are placed upon the types of materials which will be preferable.

The best suited materials are generally found between the various classes of polymers, inorganics and ceramics. The following types of polymers are suitable: polyolefins, such as polyethylene, polypropylene, and polymethylpentene; poly(halogenated olefins), such as polytetrafluoroethylene; polyvinylidene difluoride; polyamides; polyimides; polysulfones; polyacrylonitriles; polyesters; and polyphenylene oxides. Polytetrafluoroethylene (PTFE) is a particularly promising material in this respect (see the experimental section below).

The extremely high mass transfer capabilities obtainable using hollow fibre membranes, but also other kinds of tubular members such as chambers, conforming to the above-discussed criteria give rise to remarkable efficiency possibilities such as already indicated above. However, to fully utilize the potential provided by the high performance hollow fibre membranes defined according to the present invention in which the tortuosity is close to or equal to $1/\epsilon$, the present invention provides special design principles for apparatus embodying the hollow tubular members, e.g., hollow membrane fibres, which principles are based on the new understanding according to the invention of the decisive criteria for obtaining more effective and more advantageous mass transfer than was possible hitherto. The expression of these advantages are, however, not limited to mass transfer apparatuses where the membranes conforming to the above-mentioned criteria are incorporated.

In the following, these design principles will be discussed in detail.

The following features are features of general importance for a mass transfer apparatus for high transfer rate applications such as a number of high transfer rate industrial applications which have been rendered possible through the present invention:

1) The module should allow at least two inlet and two outlet connections in order to handle two separate fluids.
2) The module should allow flow of the first fluid in a direction transverse to the longitudinal of the hollow fibres,
3) The module should, for most purposes, allow large interstitial velocities of the flow of the first fluid so as to ensure high mass transfer rates and thereby minimize the total membrane area required for a given application.
4) The module should allow a short gas residence time so as to minimize the energy consumption.
5) The module should allow a large membrane area to be packed within a single module so as to ensure a large gas handling capacity for industrial applications and thereby minimize installed module costs.
6) The module should minimize channelling and bypassing by ensuring an even spacing between the fibres and mechanical stability of the fibre body.
7) The module should allow for ease of production for industrial scale applications.

Thus, in a further aspect, the invention relates to a method for transferring mass between a flow of a first fluid and a flow of a second fluid, one of the fluids, preferably the first fluid, being a gas phase and the other being a liquid phase, the method comprising contacting the first fluid with the outer surface of a plurality of hollow tubular members, at least part of the walls of the hollow tubular members comprising porous membranes with gas-containing pores and contacting the second fluid with the inner surface of said hollow tubular members, the maximum pore size of said membranes being such as to prevent direct mixing of the two fluids, the wall morphology of the membranes being so adapted that the mass transfer coefficient of the membranes with respect to the mass transfer in question is at least one tenth of the mass transfer coefficient of the gas phase, the hollow tubular members being arranged parallel to each other or at angles to each other, the plurality of hollow tubular members defining interstices therebetween through which interstices the first fluid is moved in a transverse direction relative to the longitudinal direction of the hollow tubular members.

In a still further aspect, the invention relates to an apparatus for transferring mass between a flow of a gas phase and a flow of a liquid phase, the apparatus comprising a tubular conduit having an open inlet end, at least a part of the wall of the tubular conduit comprising a plurality of hollow tubular members, at least a part of the walls of the hollow tubular members comprising porous membranes having gas-containing pores, the maximum pore size of the membranes being such as to prevent direct mixing of the gas phase and the liquid phase, the plurality of hollow tubular members defining at least one array with interstices between the members allowing flow of the gas.

It is preferred that the mass transfer coefficient of the membrane with respect to the mass transfer in question is at least one tenth such as at least one fifth of the relevant mass transfer film coefficient, and in particularly preferred embodiments of the invention, the mass transfer coefficient of the membrane with respect to the mass transfer in question is at least half the relevant mass transfer film coefficient, and is most advantageously equal to or larger than the mass transfer film coefficient. Thus, a very attractive and realistic range made possible through the present invention is where the mass transfer coefficient of the membrane with respect to the mass transfer in question is 0.5–5 times, such as 0.5–2 times, the relevant mass transfer film coefficient.

The gas pressure drop over the array of hollow tubular members is preferably at the most 4000 Pa such as at the most 3000 Pa, and in particular at the most 2000 Pa. In preferred embodiments of the present invention the gas pressure drop is at the most 1500 Pa, or better at the most 1000 Pa and preferably at the most 500 Pa which is completely realistic when utilizing hollow fibre membranes conforming with the tortuosity criteria defined above.

In all of the above-described embodiments, it is highly preferred to have a flow pattern where the first fluid flows in a transverse direction relative to the longitudinal direction of the tubular members, e.g. the hollow fibres, in particular in a direction substantially perpendicular to the longitudinal direction of the tubular members, as this will give the most efficient mass transfer between the first and the second fluids. In practice, a plurality of hollow tubular members is normally used, the tubular members being arranged parallel to each other or at angles to each other, the plurality defining an array through which the first fluid moves in the interstices between the tubular members. It will be understood that this "array" can be a relatively tightly packed configuration where the tubular members are all parallel to each other and the space for the passage of the first fluid is established by keeping the tubular members spaced from each other, but in most practical embodiments, the volumetric packing fraction of the tubular members in the array will be a relatively loose packing, such as between 0.02 and 0.8 by volume, corresponding to a void space for passage of the first fluid of between 0.98 and 0.2 by volume.

In many of the systems of the invention, a very low volumetric packing is used, but still, very high volumetric mass transfer rates are maintained. This has become possible because of the very efficient and "fast" character of the membranes selected according to the criteria according to the present invention.

In one of the most interesting embodiments of the invention, the hollow tubular meuers are hollow fibres. Thus, in the following the hollow tubular memrers are exemplified by the hollow fibres. Especially, the apparatus and the method according to the invention hereby exemplified with hollow fibres are intended to comprise all possible types of tubular members, not only hollow fibres, having at least a part of their wall constituted by a porous membrane.

The volumetric packing fraction of the fibres in the fibre array in these embodiments is between 0.02 and 0.2 by volume, preferably between 0.03 and 0.15 by volume, more preferably between 0.03 and 0.1 by volume. This corresponds to a void fraction of between 0.8 and 0.98 by volume, between 0.85 and 0.97 by volume, and between 0.9 and 0.97 by volume, respectively.

On the other hand, there are processes where a higher packing fraction will be desirable. Examples of this are processes where there are space restrictions, and where a higher packing and a lower superficial velocity will be used. For such purposes, a relatively tight volumetric packing fraction of the fibres in the fibre array of between 0.2 and 0.8 by volume may be used, e.g. between 0.3 and 0.7, such as between 0.4 and 0.65.

The volumetric packing fraction may be substantially constant throughout the fibre array, but in other important embodiments, the volumetric packing fraction varies through the fibre array. Thus, it may be advantageous that the volumetric packing fraction increases in the direction of the flow of the first fluid, whereby the first fluid will be involved in mass transfer with an increasing amount of the second fluid; this could be preferred where the equilibrium conditions do not particularly favour the complete removal of a component from the first fluid. On the other hand, it may be advantageous that the volumetric packing fraction decreases in the direction of the flow of the first fluid, namely in cases where the second fluid may become saturated by passage through the first few layers due to the higher flux caused by the higher driving force.

In preferred practical embodiments, the hollow fibres of the plurality of fibres are arranged as layers of fibres where the fibres in each layer are substantially parallel to each other and arranged at a distance from each other. One special example of this is where the fibre layers constitute a cloth having weft and warp fibres, which will favour an even distribution of the fibres. The direction of the fibres in a layer can define an angle of between 90 and 0 degrees relative to the direction of the fibres in a next layer, such as between 90 and 10 or between 90 and 20 degrees, or very often a right angle. Normally, the layers will be superimposed on each other and in contact with each other, and the direction of the fibres in a layer will then normally define an angle of between 90 and 10 degrees relative to the direction of the fibres in a next layer, so that, due to the angle, space will be established between the layers in contrast to the more compact packing which would occur if the layers were completely parallel to each other. The direction of the fibres in a layer will normally define an angle of between 90 and 20 degrees relative to the direction of the fibres in a next layer, in many cases an angle of between 90 and 30 degrees relative to the direction of the fibres in a next layer.

The angle defined between the direction of the fibres in a layer and the direction of the fibres in a next layer may decrease in the direction of the flow of the first fluid, whereby the density in the next layer will be higher than in the first-mentioned layer. This may be utilized, e.g., when preparing fibre bodies by fibre winding on a perforated or porous tube, such as explained in the following. In such a case, the fibre length may, if desired, be kept constant, the decrease of the angle compensating for the increase in diameter. It is, however, also possible to keep the angle defined between the direction of the fibres in a layer and the direction of the fibres in a next layer substantially constant in the direction of the flow of the first fluid, which means that the fibres in the outer layers of a circular fibre array will be longer than then the fibres in the inner layers. Finally, the angle may be decreased in the direction of flow of the first fluid, whereby the volumetric packing fraction will increase in the direction of the flow of the first fluid.

In a very important embodiment of a module for carrying out the method of the invention (and, also a number of other unit operations where a transverse and in particular perpendicular flow of a first fluid relative a plurality of fibres is desirable), the plurality of hollow fibres is positioned on a surface having perforations or pores or a mesh or net structure trough which the first fluid passes and flows in a transverse direction relative to the longitudinal direction of the fibre array.

Due to the extreme efficiency and "fastness" of the hollow fibre membranes meeting the criteria according to the present invention, it becomes realistic to arrange the fibres in an array inside a conduit for the first fluid so that the first fluid in the conduit flows through the fibre array, the ends of the fibers extending outside the conduit, the inlet ends and the outlet ends, respectively, of the fibers conmnicating with inlet and outlet liquid plenums, respectively. In this case, the cross section area of the conduit may be substantially unchanged at the site of the fibre array so that the superficial gas velocity, relative to the fibres, is substantially the same as the superficial gas velocity upstream and downstream of the fibre array, in other words, an excellent example of the utilization of the extreme mass transfer capabilities of fibres meeting the above criteria. While such an arrangement has been shown in the prior art, cf. EP-A 0 374 873, it would seem that most of the potential practical utilizations thereof, with low pressure drops, are possible only when utilizing the extremely efficient hollow fibre membranes conforming to the selection criteria of the present invention.

In a preferred embodiment of the invention the walls or at least a part of the walls of the tubular conduit of the apparatus according to the invention comprise a plurality of hollow fibres. It is thereby possible to expose the hollow fibres or at least a part thereof to the first fluid, i.e. the gas phase. Typically, the wall of the tubular conduit also comprise other members, such as means for keeping a desired distance between the fibres, e.g., a perforated or porous or mesh- or net structure, and means for keeping the array in a fixed position relative to other members of the conduit, however these means must allow the gas to flow in interstices between the fibers.

Thus, the perforated or porous or mesh- or net-structured surface on which the fibre array is arranged in a number of important designs may be part of a surface or wall of a conduit for the first fluid, such as a tube. Thus, in important embodiments of such a fibre module, the surface is the surface of a tubular perforated or porous fluid conduit, and each layer of hollow fibres is spirally wound on the tubular surface.

In a design embodiment of great practical importance for a large number of industrial applications, the conduit may be a tubular conduit having an open inlet end. The tubular conduit is in most practical embodiments blocked or substantially blocked at an end thereof opposite to the inlet end so that the flow of the first fluid is forced to pass from the conduit and transversely through the fibre array. The wall of the conduit or at least a part thereof comprises a plurality of fibres. In the preferred embodiment of the invention, the wall of the tubular conduit is further constituted by a perforated or porous or net- or mesh-configured tubular structure on or in which the fibres are arranged or by a self-supporting tubular interior surface of the fibre array itself.

In order to avoid bypass or channel formation and, on the whole to ensure optimum utilization of the whole area of the fibre array, the rate of transverse flow of the first fluid through the fibre array may be regulated so that it is substantially constant along the length of the fibre array in the axial direction of the tubular conduit. The regulation may be performed by applying controlled pressure differential across the fibre array along the axial length of the fibre array. The controlled pressure differential may be obtained in number of ways. One of these would comprise monitoring the pressure differential and keeping it constant in an on line pressure or vacuum regulation system, but simpler and preferred ways would be to vary the permeability of the conduit surface in axial direction, and/or to axially vary the cross-sectional area for flow of the first fluid in the tubular conduit so that a substantially constant pressure differential is thereby maintained. In connection with the latter possibility, an elegant design is where the variation of the cross-sectional area for flow of the first fluid in the tubular conduit is obtained by means of an cross section area-regulating body extending axially inside the tubular conduit. When the tubular conduit has a substantially circular cross-section, the cross section area-regulating body is suitably a solid body of revolution of a paraboloid. Alternatively, or as an adjunct thereto, the controlled pressure differential may be aided by varying the cross-sectional area for flow of the first fluid after transverse passage of the fibre array, e.g. by varying the internal dimension of an external conduit through which the first fluid is withdrawn after transverse passage of the fibre array.

Thus, in order to regulate the cross-sectional area of the external conduit is increased in the axial direction towards the outlet end thereof, and the cross-sectional area of the tubular conduit is decreased in the axial direction of the internal conduit away from the inlet end thereof.

For a number of industrial applications, such as flue gas cleaning, huge amounts of gas as the first fluid have to be treated, and the fibre array therefore become very large, e.g. of diameters of up to 2 m, such as up to 4 m, preferably up to 6 m, such as up to 8 m, in particular up to 10 m or more. In such cases, it is practical that the fibre array is constituted by a number of fibre array elements arranged adjacent to each other, each element being supplied with its own liquid inlet and outlet plenum. In this manner, the fibre array elements can be produced and shipped in sizes which are adapted to the practical transportation and mounting facilities. To rationalize the production, the fibre array elements or sets thereof may be of identical exterior design and/or of identical interior design. A suitable design for fibre array elements are tube sections, but for very large tubular designs, it will normally be preferred to construct the tubes from fibre array elements which are sections of a cylindrical surface, a number of such elements when arranged adjacent to each other along their axial edges together constituting a tube section.

The ratio between the axial length of the tubular conduit carrying the fibre array and the inlet diameter of the tubular conduit is preferably at the most 8, which will be suitable for decelerating a typical superficial gas velocity in a flue gas channel, of the order of 10–20 m/s, to a transverse superficial gas velocity through the fibre array of about ½ m/s. If a similar transverse superficial gas velocity were to be obtained in the above-mentioned inside-conduit mounted fibre array based on the same typical flue gas velocity in the flue gas channel, the diameter of the channel would have to be increased by a factor of about 5.6, hardly any realistic possibility. Corresponding to the above, a ratio between the axial length of the tubular conduit carrying the fibre array and the inlet diameter of the tubular conduit of at the most 4 is suitable for achieving a transverse superficial gas velocity through the fibre array of about 1 m/s, which, in the other design mentioned above would require an increase of the diameter by a factor 4. Other interesting ratios between the axial length of the tubular conduit carrying the fibre array and the inlet diameter of the tubular conduit are at the most 2 and at most 1, respectively.

The tubular design can be easily adapted to demanding or complex mass transfer operations by utilizing multiple fibre arrays superimposed in the direction of the transverse flow, each array having its own liquid inlet and outlet, the arrays being supplied by the same or different liquids for selective absorption of the same or different gases as the first fluid passes transversely through the superimposed arrays. In this manner, the elements can be arranged in series for removal of each individual pollutant selectively (e.g. removal of HCl by absorbent 1, removal of $SO_2$ by absorbent 2, removal of $NO_x$ by absorbent 3, removal of $CO_2$ by absorbent 4 and so on), so as to facilitate subsequent handling of individual absorbent for recovery of individual pollutants as desirable. Thus, the absorbent in a first section may be water for selective absorption of HCl and $NO_2$, the absorbent in a second section may be an alkaline sulfite or citrate solution at a pH below 8.2 for selective absorption of $SO_2$, a third section may use an absorbent containing an oxidative or reductive reactant such as $H_2O_2$, $I_2$, Fe(II)EDTA, $BrO_3^-$, $Cl_2$ etc., for selective absorption of NO and removal of residual $SO_2$, a fourth absorbent may be a hydroxide or amine solution for selective absorption of $CO_2$, etc.

The advantage of such a process is the selective absorption of several components within a single apparatus without contamination of the various absorbents with undesired components. Instead, a contaminating component can be removed in a prior stage. This eases further processing of the absorbents.

The superimposition of fibre arrays may in practice be obtained in various manner. Thus, e.g. each element may contains two or more superimposed arrays, each with its own inlet and outlet plenum; or each element contains only one array, superimposition of arrays being achieved by superimposing elements as indicated above.

The fibre array may, e.g., comprise 30–500 layers of fibres, such as 50–300 layers of fibres. In connection with fibres bodies for purification of flue gases, the fibre array will often comprises 50–200 layers of fibres, such as 50–100 layers of fibres, conforming to gas residence time required for the process.

In all the above-described embodiments, the fibres in the fibre arrays are preferably selected from the fibres showing the tortuosity characteristics described herein.

As a general rule, it is preferred that the unique potentials of the hollow fibres selected according to the invention are utilized so that each array has a packing resulting in a gas pressure drop of at the most 1500 Pa, preferably at the most 1000 Pa and more preferably at the most 500 Pa. However, even if the packing results in a pressure drop of at the most 4000 Pa, such as at the most 3000 Pa or at the most 2000 Pa, the hollow fibres may still be utilized.

In a very important practical embodiment of the proposed module design for purifying a large amount of flue gas e.g. from a coal fired power plant, the conduit for carrying the flue gas may constitute the perforated or porous surface, on to which a plurality of fibres is positioned, as prescribed above. In a practical embodiment for a flue gas duct of circular cross-section, which may be as large as 10 meter in diameter, the proposed module design can be arranged as shown in FIGS. 7–12, where several module sections (3) have been arranged in parallel for handling the large quantities of flue gas. For the ease of production of these large module sections, a module section (3) may be further segmented into module segments (S) as shown in FIG. 9. Each such segment (S) can then be produced by the methods described above for handling the first fluid and the second fluid for individual process applications. Each segment so produced can then be mechanically assembled with ease, for providing the module section (3).

In the fibre arrays, the fibres are suitably "potted" in a potting material in both ends to seal the shell side from the lumen side. The potting of fibres can be carried out in any suitable manner and such procedures are well known in the art (e.g. U.S. Pat. Nos. 3,422,008, 3,339,341, 3,442,389, 3,455,460, 3,690,465, 4,207,192, 5,264,171, EP 0562520 A1), all of which are incorporated herein by reference.

The potting material is generally in liquid form and should generally have a low viscosity when in the liquid state and a low exotherm when the liquid polymer solidifies. Low viscosity promotes penetration of the liquid potting compound between the fibres. A low exotherm prevents melting of the fibres when the liquid potting compound is cured and solidified. Further the potting compound must not lower the chemical and thermal stability of the module.

The potting material can be organic or inorganic or a mixture thereof. Suitable potting materials are well known and described in U.S. Pat. Nos. 4,369,605 and 3,422,008, incorporated herein by reference.

The fibre ends are cut by conventional techniques to expose open fibre ends in the fibre array to allow for entrance and exit of second fluid.

On the other hand, it is believed that the above-described tubular design is novel per se, and in view of its evident advantages and flexibility with respect to selection of gas velocity and regulation of pressure differential, this novel design constitutes an aspect of the present invention, irrespective of whether the fibres used are fibres selected according to the principles of the present invention with respect to their tortuosity factor characteristics, or whether the fibres are such which are suitable for mass transfer operations, but which do not possess the critical tortuosity factor characteristics. Further advantages can be expressed by utilizing multiple fibre arrays superimposed in the direction of the transverse flow as described above.

In a similar manner, the above-described design characteristics can be utilized where the hollow fibre arrays are replaced by flat membrane arrays, such as arrays of elongated chambers having one or more region(s) constituted by one or more flat membranes, where the chambers are arranged so that they provide, to the extent possible, suitably similar operating conditions as for the hollow fibre arrays. Although flat membranes will not be able to give the full spectrum of advantages which is so unique to hollow fibre membranes, it is nevertheless believed that the advantages of the above-described design principles are so important that they justify the incorporation of their use with flat membrane modules as an aspect of the present invention.

Thus, in an embodiment of the present invention the hollow tubular members are elongated chambers arranged longitudinally substantially parallel to each other, the longitudinal surfaces of the chambers having at least one region, the region(s) being constituted by at least one porous membrane having gas-containing pores.

In preferred embodiment of the present invention, the dimensions of the hollow tubular members will generally be different from the dimensions of the hollow fibre.

Thus, the void fraction in the array of chambers for passage of said first fluid is preferably between 0.2 and 0.98 by volume, but will generally be smaller than for the hollow fibre array. In preferred cases it is advantageous to arrange the chambers in a manner which results in a void fraction between 0.2 and 0.8 by volume, or in particular between 0.2 and 0.6, such as between 0.3 and 0.5 or between 0.2 and 0.4 by volume.

The void fraction is a function of the distance between the individual chambers and the dimensions of the individual chambers.

The distance between the individual chambers is preferably substantially identical through the chamber array. However, in some cases it may be advantageous to construct the array with varying distance between the chambers through the array in order to compensate for pressure differences in the first fluid, e.g, the gas phase, over the surface of the array. Compensation can, however, also be achieved by using chambers having different sizes and/or shapes.

The distance between the individual chambers in the array is preferably less than 25 mm, such as less than 10 mm, in particular between 0.1 mm and 8 mm such as between 0.5 mm and 4 mm or between 2 mm and 6 mm.

The largest cross-sectional dimension of the chambers in the direction transverse to direction in which the first fluid moves and perpendicular to the longitudinal dimension of the chambers is preferably less than 20 mm, such as 0.1–5 mm, in particular 0.3–3 mm, such as 0.3–1.5 mm or 0.5–3 mm.

The largest cross-sectional dimension of the chambers in the direction parallel to the direction in which the fluid moves and perpendicular to the longitudinal dimension of the chambers is at the most 25 cm, such as at the most 10 cm, in particular between 1 and 10 cm, such as between 1 and 6 cm or between 4 and 10 cm.

In a preferred embodiment, the elongated chambers are arranged as shown in FIGS. 13 and 14. The horizontal arrow indicates the direction in which the first fluid moves and the two vertical arrows indicates the direction in which the second fluid moves. The membrane surfaces are not explicitly shown in the figures, but one or more membrane surface(s) is/are preferably arranged on each of the sides parallel to the direction in which the first fluid moves. The enlarged section shows the chambers and the outlet plenum.

In order to obtain a rigid array of chambers, especially where a large part of the individual chamber surface is constituted by a flexible flat membrane, the individual chambers or adjacent chambers may be supported by a supplementary structure.

Thus, in a preferred embodiment the chambers comprise a perforated-, porous-, mesh-, or net structure in order to control the distance between opposing surfaces of the chambers. The rigidity can also be obtained by arranging the array of chambers on a surface having perforations or pores or having a mesh or net structure, e.g., as illustrated in FIG. 10. However, the structure has to be constructed so that first fluid can pass and flow in a transverse direction relative to the longitudinal direction of the chambers. In particular, the perforated or porous or mesh- or net-structured surface is a part of the wall of a conduit for the first fluid.

In a preferred embodiment, the chamber arrays are arranged in manner similar to the above-described arrangements of hollow fibre arrays. This applies in particular to superimposition of arrays. The above-described principles for the construction of a conduit for the first fluid around the hollow fiber array(s) also applies to the arrays of elongated chambers. Thus, conduit sections are consequently constituted by chamber arrays.

As mentioned above, when selecting the hollow membrane fibres on the basis of the criteria defined herein, exceptionally low membrane area requirements per cubic meter of gas phase handled will prevail for absorption processes, permitting hitherto unseen efficiencies in the absorption.

In an absorption process where a gas component is absorbed from a gas mixture into a liquid by a chemical reaction, the membrane area, $A_m$, required to handle a gas stream, G, in $m^3/s$, is defined by Equation 9:

$$A_m/G = \ln((C_1 - C^*_1)/(C_2 - C^*_2))/K_o \qquad (9)$$

wherein $C_1$ and $C_2$ are the inlet and outlet gas phase concentrations, respectively, of the component in question, $C^*_1$ and $C^*_2$ are the equilibrium concentrations of the gas component in question over the liquid phase at the gas inlet and the gas outlet, respectively, and $K_o$ is the overall mass transfer coefficient, as defined by Equation 2. When the method of the invention is applied to obtain an absorption efficiency of at least 95% ($C_1/C_2$ equal to or greater than 20), the membrane area requirement per $m^3/s$ of gas handled can easily be as low as at the most 200 $m^2/(m^3/s)$ where each $C^*$ is at most 0.05.C, or as low as at the most 500 $m^2/(m^3/s)$ where each $C^*$ is greater than 0.05.C. Thus, realistic membrane areas per $m^3/s$ of gas handled are at most 100 $m^2/(m^3/s)$ where each $C^*$ is at most 0.05.C, or at most 300 $m^2/(m^3/s)$ where each $C^*$ is greater than 0.05.C, or at most 75 $m^2/(m^3/s)$ where each $C^*$ is at most 0.05.C, or at most 150 $m^2/(m^3/s)$ where each $C^*$ is greater than 0.05.C, and even lower, such as at most 50 $m^2/(m^3/s)$ where each $C^*$ is at most 0.05.C, or at most 100 $m^2/(m^3/s)$ where each $C^*$ is greater than 0.05.C or, with hollow fibre membranes well adapted in accordance with the above criteria and arranged in suitable apparatus (which will be discussed further below), as low as 10–30 $m^2/(m^3/s)$ where each $C^*$ is at most 0.05.C, or 30–90 $m^2/(m^3/s)$ where each $C^*$ is greater than 0.05..C.

Thus, in another aspect, the present invention relates to a process where a mass is transferred between a flow of a first fluid and a flow of a second fluid, one of the fluids being a gas phase and the other phase being a liquid phase, the first fluid being contacted with the outer surface of a plurality of porous membranes in the form of hollow fibres with gas-containing pores and the second fluid being contacted with the inner surface of said membranes, the maximum pore size of said membranes being such as to prevent direct mixing of the two fluids, the process being an absorption or a desorption process in which a component is removed from a gas or liquid phase, respectively, wherein, with reference to Equation 9 herein the membrane area required per cubic meter of gas phase handled per second, $A_m/G$, for $C_1/C_2$ equal to or greater than 20, $C_1$ being the inlet concentration, in the gas, of the component in question, and $C_2$ being the outlet concentration, in the gas, of the component in question, is at most 200 $m^2/(m^3/s)$ where each $C^*$ is at most 0.05.C, or is at most 500 $m^2/(m^3/s)$ where each $C^*$ is greater than 0.05.C.

In particular, the invention relates to the process described above, where the fibres are arranged parallel to each other or at angles to each other, the plurality of fibres defining a fiber array through which the first fluid moves in interstices between the fibres in a transverse direction relative to the longitudinal direction of the hollow fibres, and the pressure drop over said fibre array being at the most 1500 Pa, such as at the most 1000 Pa, in particular at the most 500 Pa. In some cases, especially in desorption processes, the pressure drop may be even higher, e.g., up to 4000 Pa, such as up to 3000 Pa or up to 2000 Pa.

The method of the present invention is particularly well suited for applications where the first fluid is a gas and the second fluid is a liquid. A good example hereof is the removal of $SO_2$ from a flue gas by absorption (with attendant chemical reaction) into a sulfite solution.

As already indicated above, the method of the invention is very well suited to systems wherein the first fluid is a gas mixture and the second fluid is a solution capable of absorbing one or more component(s) of the gas mixture, and in this connection the solution in question may contain a reagent which undergoes a chemical reaction with a component of the gas mixture. As also indicated above, a gas mixture to which the method may suitably be applied is a combustion flue gas, i.e. a flue gas arising from the combustion of combustible materials such as fossil fuels (coal, coke, oil, biomass and the like) or the combustion/incineration of refuse, e.g. industrial or domestic refuse containing paper, wood, plastics and the like; a fuel gas from gasification of bio fuels, or any industrial waste gas.

Such combustion processes often give rise to gas mixtures which contain significant levels of environmentally undesirable gases such as $SO_2$, $NO_x$ (normally a mixture of, predominantly, NO and $NO_2$), HCl, HF, $SO_3$, $CO_2$ or other gaseous products which are, or which contain, acid-forming gases, and the method is well suited to the removal of such species from a combustion exhaust gas (e.g. a flue gas), e.g. using—as a second fluid—a basic solution which can react with the acid-forming gas, e.g. an aqueous solution of a base such as an alkali metal hydroxide, alkali carbonate, alkali metal citrate or the like.

In case of removal of $SO_2$, a suitable absorbing fluid (second fluid) is, as already indicated, an aqueous alkali metal sulfite solution, in particular an about 0.3–1.5 M, such as a 0.5–1 M, solution. By adjusting the pH of such a solution, e.g. by lowering the pH, it is possible to adjust the selectivity of the solution with respect to absorption of other species such as $CO_2$.

Likewise, it will clearly be possible to remove a basic gas such as ammonia form an industrial waste gas into an acidic medium, e.g. a dilute mineral acid such as sulfuric acid.

In applications according to the method of invention, the pores of the porous membrane are—owing to the nature of the mechanism by which the hollow fibre membrane functions—in general gas-containing. However, apart from the gas present in the pores, it is clear that there is a possibility of introducing a species capable of reacting with the component (components) which is transported across the membrane (a reactant) and/or introducing a catalyst capable of promoting a chemical transformation of the migrating species, into the pores of the membrane for certain applications.

Likewise, it is clear that the catalyst may possibly be laminated on a surface of the hollow fibre.

Thus, in a process for the removal of NO from a gas mixture, the low solubility of NO in aqueous media makes it desirable to perform a prior oxidation of NO to $NO_2$ which has a higher solubility. For this purpose, an oxidative catalyst such as a transition metal (Pd, Ag, Co, Cu, Ni, Mn, Cr, Cd, Fe, etc.) or a transition metal oxide ($CuO$, $Co_3O_4$, $Fe_2O_3$, $NiO$, $V_2O_5$, $V_2O_3$, $TiO_2$, $MnO$, $Cr_2O_3$) may be laminated or impregnated on the membrane for catalysing the oxidation of NO to $NO_2$. The catalytic oxidation is then followed by absorption of the $NO_2$ formed in a suitable absorbent such as water, an alkaline sulfite solution etc.

In the special case where the process is removal of $SO_2$ from flue gas from a power station burning fossil fuel, the method of the present invention will permit a membrane area requirement for achieving a removal efficiency of 95% of at the most 200 $m^2$ per MWe, and realistic membrane area requirements achievable by effective utilization of the principles of the invention will be at the most 100 $m^2$ per MWe or better, such as at the most 75 $m^2$ or preferably 50 $m^2$ per MWe or even down to 10–30 $m^2$ per MWe, thus corresponding to efficiencies which have, to the Applicants' best knowledge, never been achieved in the prior art.

In the above-mentioned embodiments, the performance criteria related to Equation 9 can in most cases be fulfilled by using the hollow fibre arrays and the flat membrane arrays described above.

In general, the method of invention utilizing hollow membrane fibres conforming with the tortuosity characteristics is suited to any kind of process involving the transfer (stripping) of one or more gaseous or volatile component(s) from a liquid phase to a gas phase. Examples hereof are the transfer of $SO_2$, $SO_3$, $NO_x$, HCl, $CO_2$, $H_2O$, alcohols, halogenated hydrocarbons, etc. from liquid mixtures to a gas.

It is for example contemplated that water can be stripped from a solution containing thermosensitive compounds into a gas phase at temperatures below the boiling point of the solution. In this manner, thermosensitive compounds or compositions such as fruit juices, aroma compounds, enzymes, proteins, lipids, saccharides, pharmaceuticals, polymers, etc. can be concentrated without thermal degradation.

For efficient operation of the contacting apparatus, the temperature should generally be as high as the solution allows, such as for example 25–75° C.

It is often preferred to employ an inert stripping gas such as $N_2$, Ar, He, $CO_2$ in order to avoid chemical degradation of the thermosensitive compound or composition.

An efficient mass transfer apparatus for such applications is provided by use of a hollow membrane fibre specified according to the invention. However, most known module designs cannot provide a sufficiently small gas residence time to avoid saturation of the gas phase. Hence, the efficiency of such a mass transfer apparatus is often limited by the module design. Example 2 below illustrates these considerations.

It is further contemplated that a membrane mass transfer process may be used for the continuous removal of ethanol from fermentation broths, e.g. for the preparation of non-alcoholic beer, or in a continuous process for the biological manufacture of industrial ethanol.

Thus, the production of ethanol by fermentation of sugars, starch and biomass (wood, municipal waste etc.) is generally inhibited by ethanol, i.e. the production rate is limited by the ethanol concentration and drops during fermentation. It is well known that the fermentation stops at a certain ethanol concentration and efforts have therefore been directed to eliminate the inhibition by continuous recovery of ethanol. The present mass transfer method and module design could be used in a process to accomplish this and for minimization of the energy consumption for product recovery. The process is illustrated in FIGS. 1–2.

The content of a fermenter, namely the fermentation broth containing substrate solution (carbon and nitrogen sources, minerals etc.) and ethanol-producing microorganisms (such as yeast cells), is continuously fed to the mass transfer apparatus according to the present invention as the second fluid, optionally after having been heated in a heater. An inert gas such as $N_2$, $CO_2$, He, or Ar passes the module as the second fluid on the other side of the membrane. The ethanol and some water evaporates from the second fluid and diffuse through the membrane into the first fluid (the inert gas) as permeate. The permeate is recovered by condensation and the inert gas stream is recirculated to the contact apparatus. The inert gas is used in order to maintain the anaerobic conditions in the fermenter (e.g. to avoid oxidative degradation of ethanol and substrate). Nonvolatiles, such as the substrate and microorganisms, do not evaporate and are recycled to the fermenter after make up of lost water as well as substrate components consumed by the microorganisms.

The separation is carried out at a temperature close to the fermentation temperature, which depends on the actual microorganism used. Fermentations based on yeast (*Saccharomyces cerevisiae, Saccharamyces carlsbergensis* etc.) and bacteria of the genus Zymomonas generally have an optimum fermentation temperature of about 30° C. and will ferment up to a temperature of about 40° C. Fermentations are exothermic processes, and the temperature sensitivity of these microorganisms means that cooling may have to be applied during the fermentation. This is difficult or expensive especially in warm climates. In the proposed process, the first fluid is cooled by the evaporation in the membrane contactor.

The fermentation temperature is generally between 55–69° C. for fermentations based on cultures of anaerobic thermophilic bacteria such as *Clostridium Thermocellum, Clostridium Thermohydrosulfuricum, Clostridium Thermosaccharolyticum, Thermoan-aerobium Brockii, Thermobacteroides Acetoethylicus, Thermoanarobacter Ethanolicus* etc. An external heating unit such as a unit having a heat pump, where the heat absorption part is connected to a waste heat part, e.g., from another apparatus, or a solar cell etc, may be used as the extra heat supply.

The maximum ethanol concentration is about 10 w/w % for yeast and Zymomonas strains, while it may be as low as only 0.5–1.0 w/w % for certain anaerobic thermophilic bacteria. The optimum pH is in the range 4–7.5 for yeast and Zymomonas.

The concentration of the ethanol recovered corresponds to the vapour-liquid equilibrium in the pore mouth, which is a function of the ethanol concentration in the feed. Generally, the concentration factor defined as the ratio of the concentration in the permeate to the average bulk concentration in the feed will be in the range from 1 to 8, if the concentrations are measured in % by weight.

It is also possible to use superimposed membrane arrays for fractionation. Thus, superimposed membrane arrays (a distillation column based on membranes) may be applied in combination with the ethanol stripping unit described above in order to form a column for further fractionation/purification of the permeate.

The substrate solution from the fermentation process above is fed to a first membrane array, where it is contacted with an inert stripping gas. The inert gas containing permeate is heat-exchanged with the liquid feed and then passes to a condensing unit, where the permeate is condensed. Such a membrane based column is shown in FIG. 3. The ethanol-enriched condensate is fed to the next membrane array after heat exchange with the outlet inert stripping gas and heating in the second heating unit. The liquid feed retenate from the second stage is recirculated to the first stage. In this way the multiple membrane sections form a membrane-based stripping column with n equilibrium stages.

Some limitations exists on the maximum allowable ethanol concentration for the liquid side. For a nominal (average) pore size of 0.2 $\mu$m (maximum pore size about 0.6), the maximum ethanol concentration will be about 40 to 50 w/w %, which will result in a permeate concentration of 75%. A smaller pore size for the following stages, may therefore be beneficial.

The membrane used for the last stages may be a nonporous pervaporation membrane for production of pure ethanol (99.95%) for liquid automobile fuels.

Likewise, the membrane stripper may be combined with a conventional distillation column and/or a pervaporation unit.

DESCRIPTION OF THE DRAWINGS

FIG. 7 illustrates a tubular design of the novel type discussed above, comprising a permeable, e.g. perforated, tubular conduit 1 having an inlet end 12, in which a solid-walled body 2 regulates the cross-sectional area for the flow of the gas entering the conduit, thereby contributing to ensuring a uniform gas distribution or pressure differential for the transverse flow (illustrated with curved arrows) of the gas through hollow membrane arrays of membrane array elements 3 having liquid inlets 4 communicating with an inlet manifold 5 and liquid outlets 6 communicating with an outlet manifold 8. The gas which has passed transversely through the membrane array elements is collected in a gas conduit 7 the walls 9 of which are so dimensioned that they contribute to the uniform gas differential through the membrane array elements by regulating the cross-section area for gas flow, such as shown. In a very practical embodiment of the design for purifying large amount of flue gas, e.g., from a coal fired power plant, the conduit in case of a circular flue gas duct may be as large as 10 m. The figure also show how several module sections 3 can be arranged in parallel for handling the large quantities of flue gas.

FIG. 8 is a cross section of the apparatus of FIG. 7 showing individual module segments S.

FIG. 9 illustrates how a module section 3 may be further segmented into module segments S for ease of production and transport. The figure also shows the liquid inlets 4 and outlets 5. FIG. 10 shows such a module segment S. The cut-way portion illustrates how the fibres F are arranged in the segment. FIG. 11 illustrates a cross-section (A—A) of the module segment in FIG. 10. FIG. 12 is an expanded view of FIG. 11 for a hollow fibre array, where the fibre ends are collected liquid plenums 10, the fibres F being potted so that the fibres have interstices I for the flow of the gas therebetween.

FIGS. 13–16 illustrate a tubular conduit 1 with a chamber array according to the invention arranged transverse to the axial direction of the tubular conduit. FIG. 13 illustrates the gas flow in the interstices between the chambers in a transverse direction relative to the longitudinal direction of the chambers as indicated by the horizontal arrow. The vertical arrows indicate the direction of the liquid flow into the liquid inlet 4 and from the liquid outlet 6. The expanded view of a section of FIG. 13 illustrates the individual chambers and the direction of the gas (first fluid—horizontal arrows) and liquid (second fluid vertical arrows). FIG. 14 illustrates the array of chambers F having interstices I therebetween. FIG. 15 is a side view of the chamber array arranged inside a conduit for the gas, the ends of the chambers extending outside the conduit, the inlet ends and outlet ends, respectively, communication with inlet and outlet plenums 10, respectively. The direction of the gas- and liquid flows are indicated by the horizontal and vertical arrows, respectively. FIG. 16 is an end view of the conduit of FIG. 15.

FIG. 19 is a side view of the test cell for the set-up of FIG. 18.

FIG. 20 is a end view of the test cell for the setup of FIG. 19.

EXPERIMENTAL SECTION

Characterization of Membranes

Table 1 below gives results obtained in the tests explained below for five different flat film membranes (3–7) and two different hollow fibre membranes (8–9). The table also contains literature data for two polytetrafluoroethylene (PTFE) membranes for which the tortuosity factor was determined by Prasad, Kiani, Bhave and Sirkar (Journal of Membrane Science 26, 79–97, 1986) in connection with extraction of acetic acid through liquid-filled pores into xylene or methyl isobutyl ketone.

Figure 1:
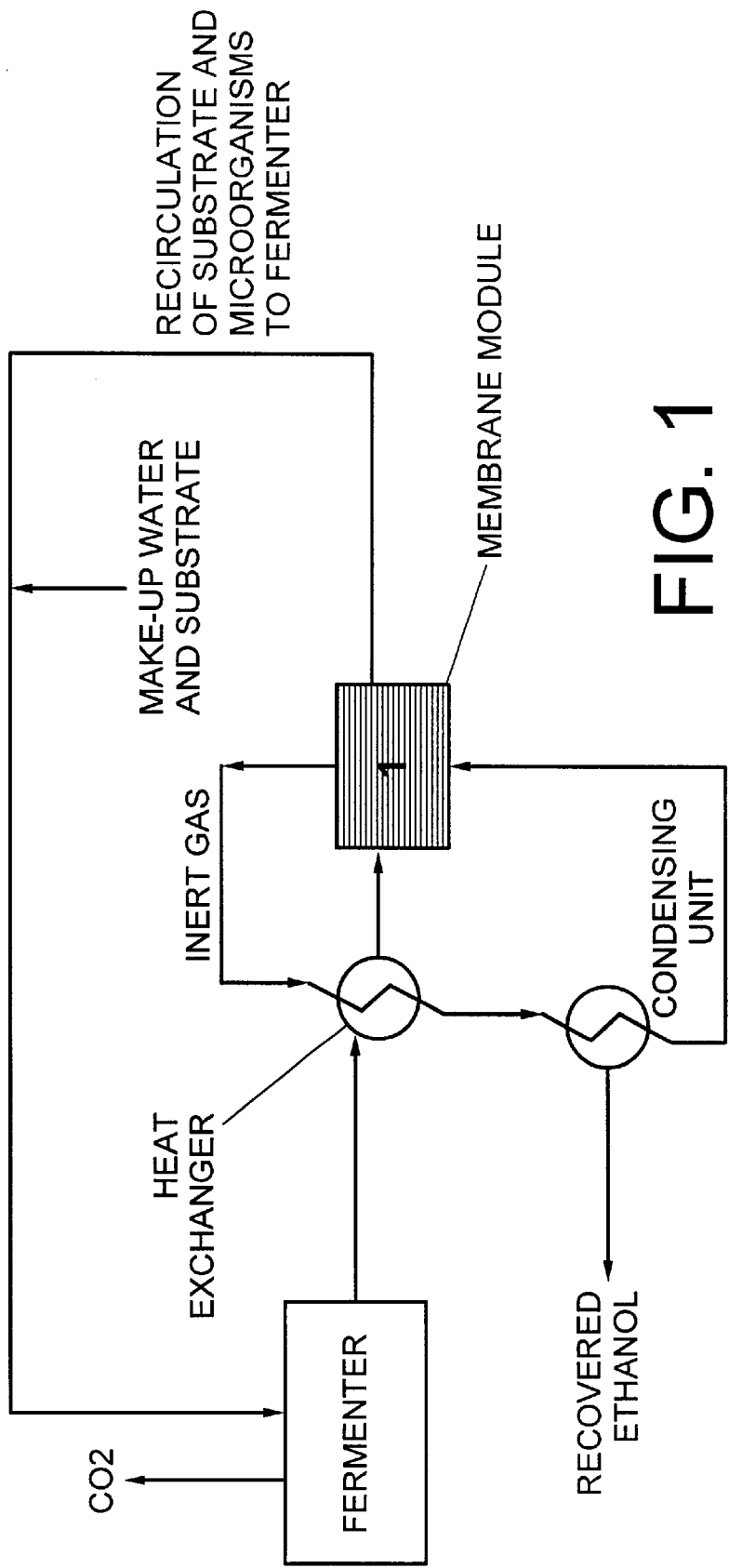
FIG. 1 illustrates the above-described process for continuous recovery of ethanol from a fermentation broth. An inert gas, such as $CO_2$, is fed to the mass transfer apparatus according to the present invention as a first fluid. The content of the fermenter, i.e. the ethanol containing substrate solution and ethanol producing microorganisms are continuously fed to the mass transfer apparatus as the second fluid after heat exchange with the first fluid. The ethanol and some water evaporates from the second fluid and diffuse through the membrane into the first fluid (the inert gas) as permeate. The permeate is recovered by condensation and the incoming second fluid from the fermenter. Nonvolatiles, such as the substrate and microorganisms are recycled to the fermenter after make up of water and substrate.
Figure 2:
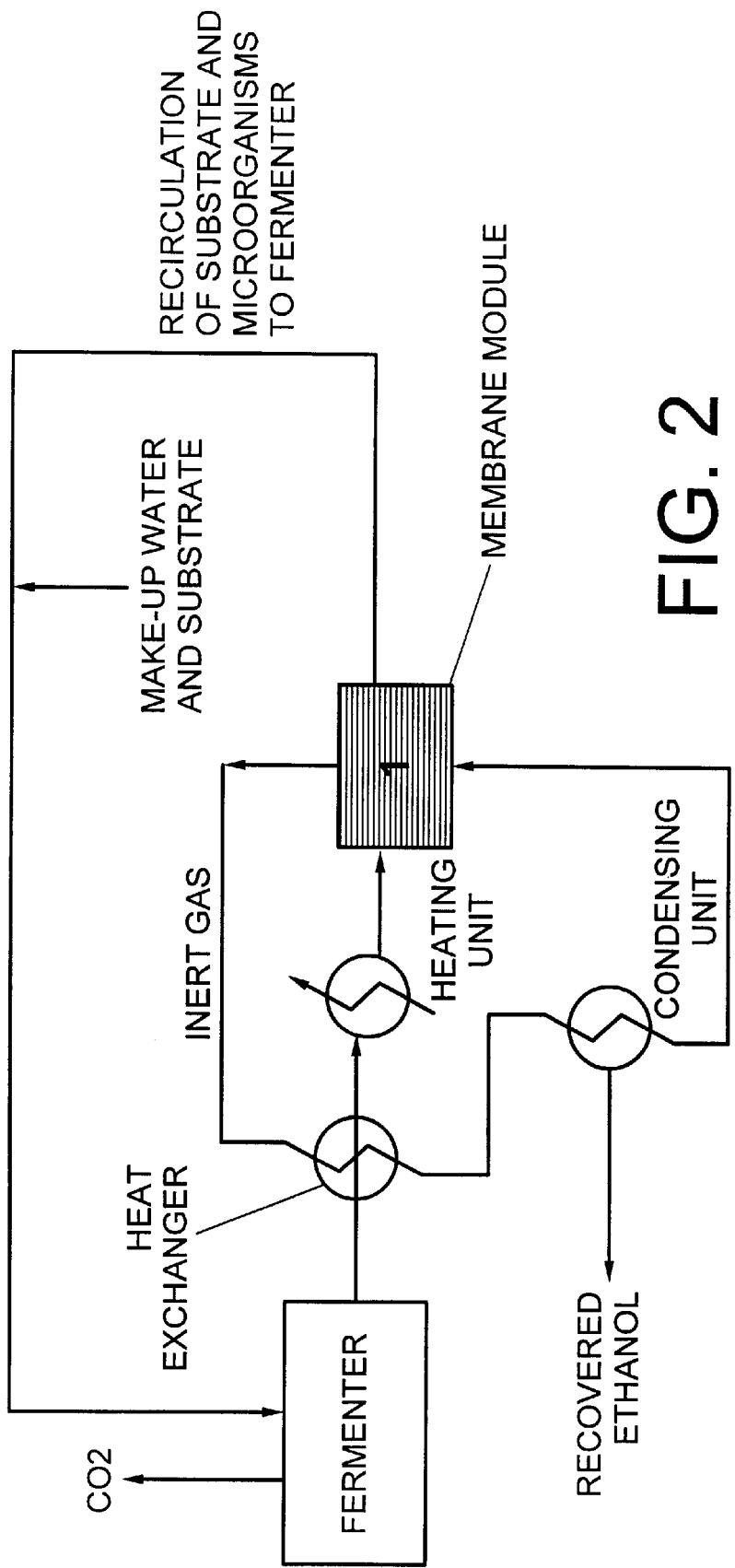
FIG. 2 illustrates a process similar to the process illustrated in FIG. 1, but where heating means for the first fluid is introduced.
Figure 3:
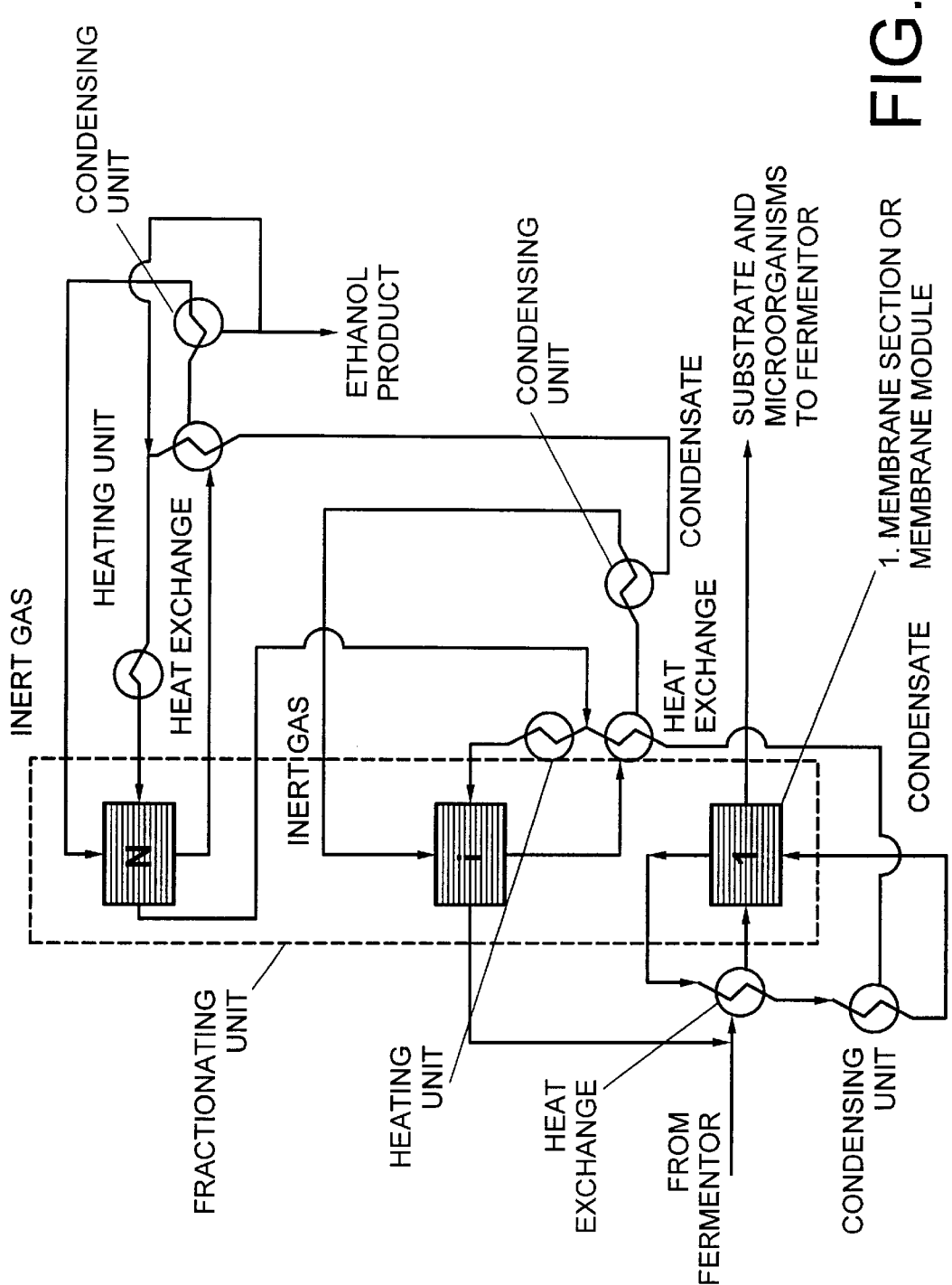
FIG. 3 illustrate how a membrane based column for the process in FIGS. 1–2 is formed by superimposing membrane arrays according to the present invention. The substrate solution from the above-mentioned fermentation process is fed to the first membrane array, where it is contacted with an inert stripping gas. The inert gas containing permeate is heat exchanged with the liquid feed and is then passed to a condensing unit, where the permeate is condensed. The ethanol enriched condensate is fed to the next array after heat exchange with the outlet stripping gas from the second membrane array and heating in the second heating unit. The liquid feed retenate from the second array is fed back to the first membrane array.
Figure 4:
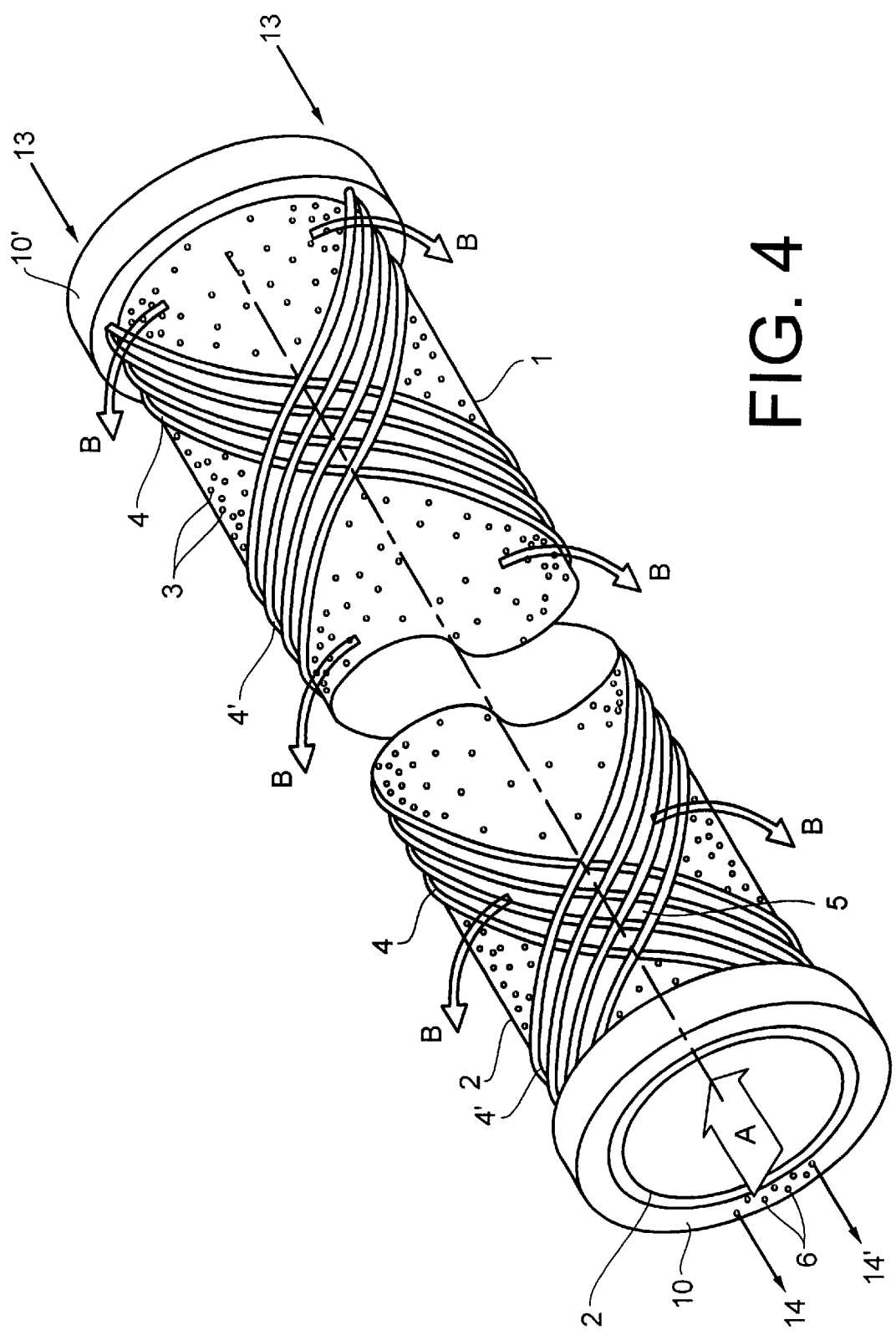
FIG. 4 illustrates a tubular hollow fibre array element 1 according to the invention. On a tube 2 of e.g. stainless steel perforated with perforations 3, two layers 4 and 4' of parallelly wound hollow fibres, preferably polytetrafluoroethylene fibres of the type discussed above, are shown. It will be understood that in a practical embodiment, a much higher number of layers will be applied, confer above. The perforations 3 in the tube will normally correspond to the voids of the fibre array, which means that the fluid passing through the perforations will be subject to substantially the same linear gas velocity through the surface of the tube as through the fibre array. The tube could also, e.g., be made of porous SiC or any other suitable porous material. The fibres are wound on the tube at an angle of about 45 degrees relative to the longitudinal axis of the tube, which means that the two layers will cross at e.g. 5 at an angle of about 90 degrees. At each end of the tube, the fibre ends are exposed in a flange 10 and 10', respectively. The fibres have been arranged in the flange by casting ("potting") the flange of e.g. epoxy or polypropylene or any of the membrane materials mentioned above in a castable form around the fibre layers and then cutting to expose the open ends 6 of the fibres. A fluid, e.g. an alkaline solution, is introduced in the fibre layers at 13 and 13' and leaves at 14 and 14'. A gas, e.g. flue gas from the combustion of fossil fuel, is introduced to the interior of the tube as indicated by an arrow A and exits through the perforated surface of the tube 2 as shown by arrows B, transversely and substantially perpendicularly to the fibre layers 4 and 4', thereby ensuring a highly efficient gas/liquid contact. The gas is then preferably collected in a suitably designed volute which then discharges the gas for further processing or to the stack.
Figure 5:
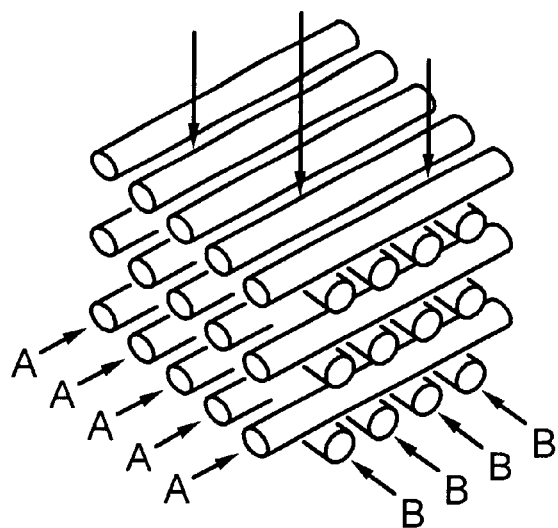
FIG. 5 illustrates superimposed layers of hollow fibres, where two different fluids (A and B) can be conducted through the lumens of the fibres, as indicated, whereas a flow of a gas can be passed transversely through the fibres from above, perpendicular to the longitudinal direction of the fibres, as indicated by the vertical arrow.
Figure 6:
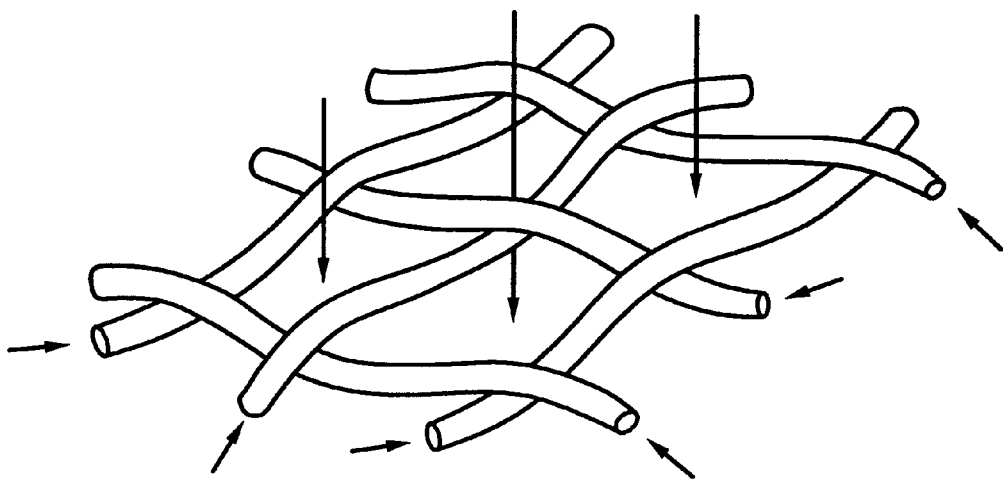
FIG. 6 illustrates a situation similar to the one in FIG. 5, but where a woven array of hollow membrane fibres is used.
Figure 9:
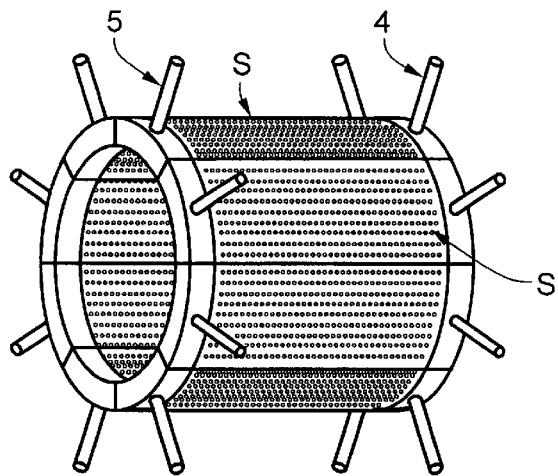
FIGS. 9–12 illustrate details of the apparatus shown in FIGS. 7–8.
Figure 10:
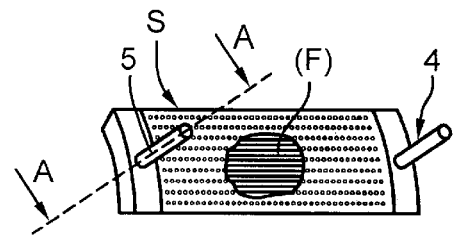
Figure 11:
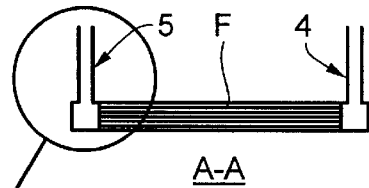
Figure 12:
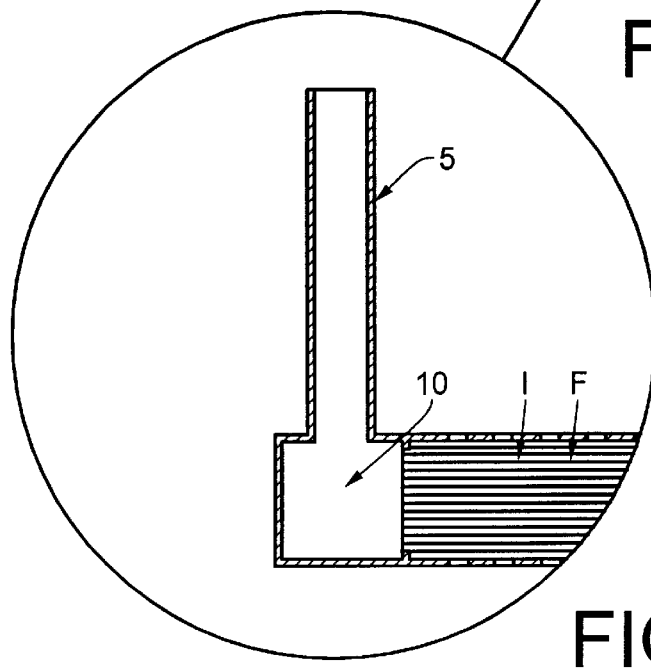
Figure 17:
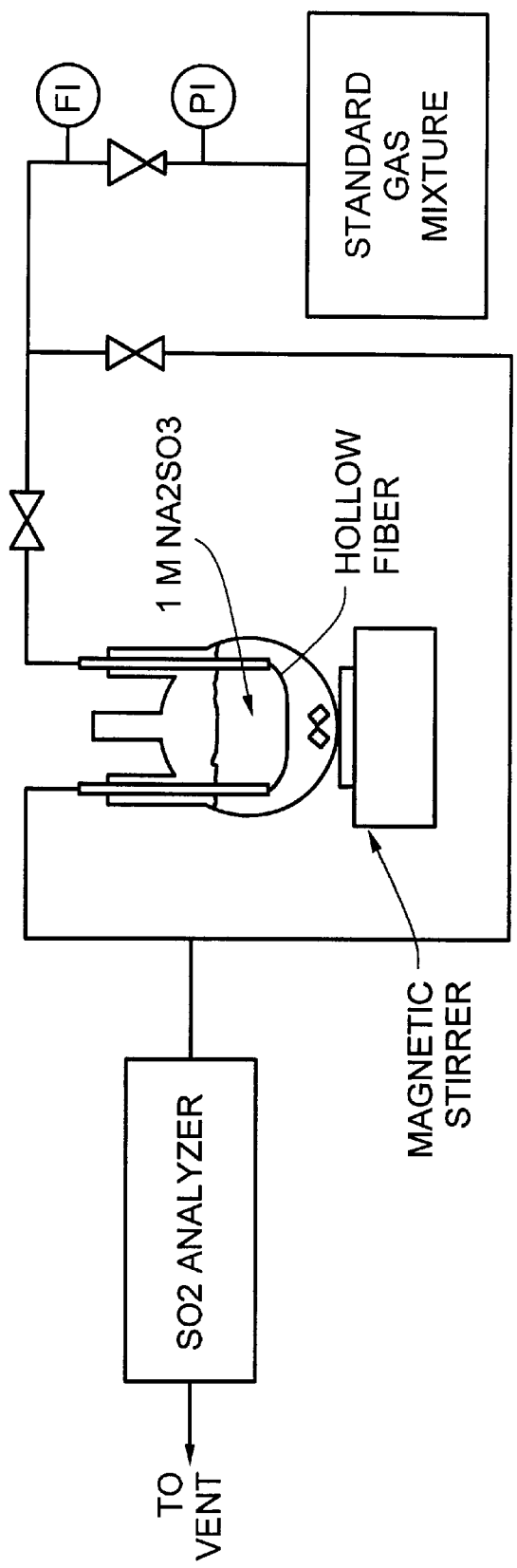
FIG. 17 illustrates the experimental setup for the determination of mass transfer coefficient and tortuosity factor of a single fibre.

The hollow fibres were tested in the experimental set up shown in FIG. 17. A length of 104–173 mm of the hollow fibre in question was fastened in a tube fitting by an epoxy resin to provide connections for gas flow. The hollow fibre and connections was placed in a closed stirred vessel containing a 1 M sodium sulfite solution. A standard gas mixture containing dilute $SO_2$ (1710 ppm v/v in $N_2$) was supplied to the lumen of the fibre. The gas flow and effective hollow fibre length was adjusted to avoid any physical or chemical saturation phenomena. The phases were stabilized until pressure equilibrium over the membrane was approached. Both phases were at ambient temperature (293° K.) Further, the assumption of negligible liquid side resistance was checked at a high gas flow rate by increasing the stirrer speed. The $SO_2$ analyzer (Hartmann-Braun UV Analyzer) was calibrated to the low gas flow rates by a three point calibration procedure. The $SO_2$ flux was then determined by measurements of the inlet and outlet concentrations at various gas flow rates. The effective membrane area was calculated on basis of the inner diameter. The gas flow was measured and controlled by a mass flow controller, which initially was calibrated by a soap bubble flow meter. The membrane mass transfer coefficient $k_m$ and the tortuosity factor could then be determined from the equations 1–8.

A similar method was used for measuring the tortuosity for at membranes given in Table 1.

TABLE 1

Membrane characteristics and measured tortuosity factors. *are data from Prasad et al, 1986.

| Membrane | Material | $\epsilon$ | t $\mu$m | $r_p$ $\mu$m | $\tau$ |
| --- | --- | --- | --- | --- | --- |
| 1. Goretex 2* | PTFE | 0.78 | 64 | 0.2 | 1.21 |
| 2. Goretex 1* | PTFE | 0.50 | 51 | 0.02 | 1.82 |
| 3. Durapore | PVDF | 0.65 | 110 | 0.20 | 2.36 |
| 4. Enka 1EPP | PP | 0.75 | 100 | 0.10 | 2.07 |
| 5. Enka 2EPP | PP | 0.75 | 145 | 0.20 | 2.17 |
| 6. Celgard 2400 | PP | 0.38 | 25 | 0.02 | 6.84 |
| 7. Celgard 2500 | PP | 0.45 | 25 | 0.04 | 4.19 |
| 8. Microdyne fiber di/do = 0.6/1.0 | PP | 0.75 | 200 | 0.20 | 2.65 |
| 9. Microdyne fiber di/do = 1.8/2.8 | PP | 0.75 | 500 | 0.20 | 2.03 |

Figure 18:
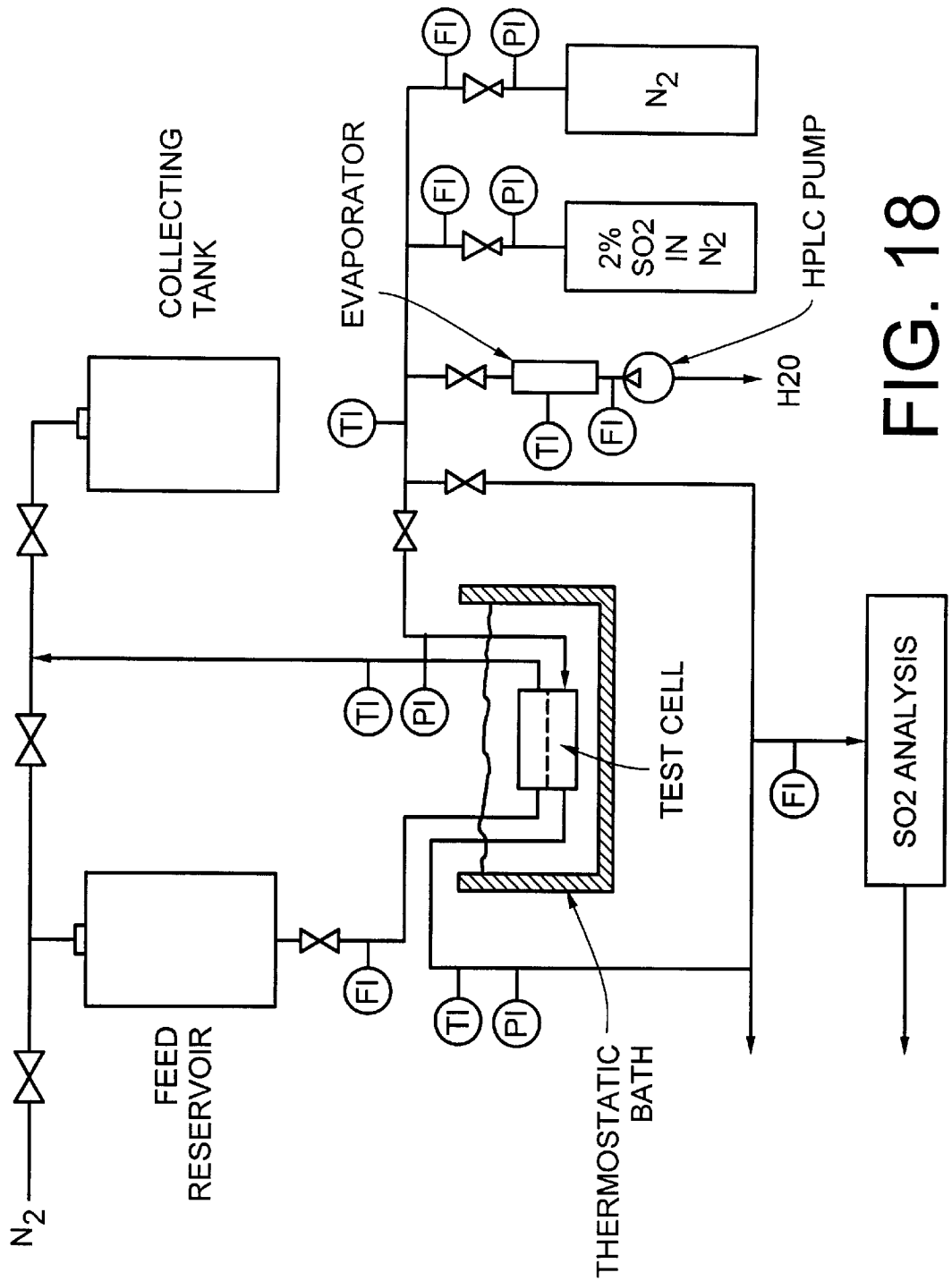
FIG. 18 illustrates the experimental setup for the determination of mass transfer coefficient and tortuosity factor of a membrane.

The experimental apparatus used in the laboratory for these measurements is shown in FIG. 18. A membrane was placed between the two frames in the test cell shown in FIGS. 19 and 20. Each frame had three flow channels of 1 mm height, 5 mm width and 80 mm long, resulting in an effective membrane area of 12 $cm^2$. The test cell was placed in a thermostated water bath at a temperature of 24° C. An aqueous 1 M sodium sulfite solution was fed to the test cell at the position denoted liquid in. A gas mixture of 1000 ppmv $SO_2$ in nitrogen was mixed by diluting a standard gas of 2% $SO_2$ in $NO_2$ with $NO_2$ until the reading on the $SO_2$ analyzer showed the desired $SO_2$ concentration (Hartmann-Braun UV-analyzer). After the desired concentration was obtained, the gas was fed to the test cell at the position denoted gas in. The gas and liquid flows were measured by Fischer-Porter rotameters and controlled by needle valves. The rotameters were initially calibrated at the delivery pressure used in the experiments (5.8 baro) by two different gas meters (wet and dry). The gas flow was varied between 2.8 and 10.5 l(0° C., 1 atm)/min. The assumption of negligible liquid side resistance was checked for each membrane by varying the liquid flow at the maximum gas flow. During the measurement the liquid flow rate was kept constant at 20 ml/min., giving a L/G ratio varying between 1.9 to 7.1 1/$Nm^3$. $SO_2$-flux and the overall mass transfer coefficient were then determined by measurements of the inlet and outlet $SO_2$ concentrations at various gas flow rates. The membrane mass transfer coefficient, $k_m$, was determined by measurements of the $SO_2$-flux and the overall mass transfer coefficient at various gas flow rates for 1, 2, and 3 membranes of same type, stacked on top of each other. It was shown statistically that the interfacial resistance between the membranes was negligible and that the resistance in the gas phase was not affected by the stacking of membranes. Thus the total resistance ($1/K_o$) was hereby increased in a controlled manner by $(n-1)/k_m$, where n refers to the number of membranes stacked. Hence, the membrane mass transfer coefficient could a be determined from:

$$\frac{1}{k_o} = \frac{1}{k_g} + \frac{n}{k_m} \quad (9)$$

$$\Updownarrow$$

$$\frac{1}{k_o}\bigg|n \text{ membranes} - \frac{1}{k_o}\bigg|1 \text{ membrane} = \frac{n-1}{k_m}$$

and the tortuosity factor could then be determined from equation 3.

Several other available membranes were also tested by the method described above, and the measured tortuosity factors were found to be in substantial agreement with data reported in the literature.

Figure 21:
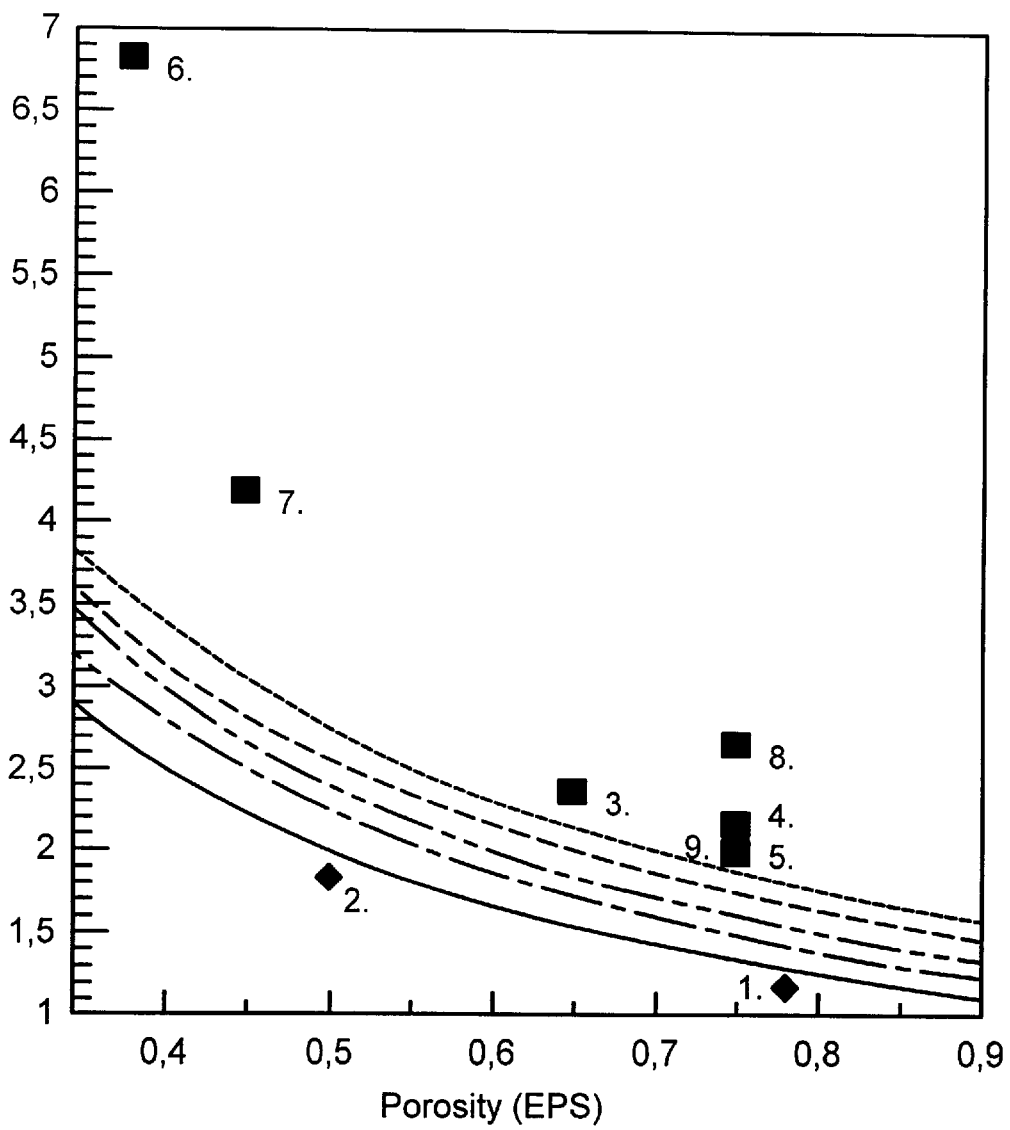
FIG. 21 shows the tortuosity factors-porosity relationship for a number of membrane materials.

The data reported in Table 1 of measured tortuosity factors and data reported in literature for tortuosity factors are shown plotted in FIG. 21 as a function of porosity. It will be seen that only the literature data reported for PTFE membranes (Prasad et al. 1986) come close to the tortuosity/porosity relation of $1/\epsilon$. The tortuosity/porosity data for membrane 3 (1.53), for membranes 4, 5 and 9 (1.55, 1.63 and 1.52, respectively), 6 (2.60), 7 (1.89) and 8 (1.99) are all higher than the critical value of 1.4.

Comparative Example 1

Table 2 below shows examples of membrane mass transfer coefficients for $SO_2$ at 293.15K for various combinations of parameters.

TABLE 2

$k_m$ for $SO_2$ at 293.15 K for various combinations of wall morphology

| Fiber no. | $\epsilon$ | t, $\mu$m | $\tau$ | $r_p$, $\mu$m | $k_m$, cm/s |
|---|---|---|---|---|---|
| 1 | 0.75 | 200 | 2.65 | 0.20 | 1.48 |
| 2 | 0.75 | 500 | 2.02 | 0.20 | 0.78 |
| 3 | 0.78 | 60 | 1.21 | 0.20 | 10.52 |
| 4 | 0.78 | 60 | 1.21 | 0.50 | 12.39 |
| 5 | 0.75 | 30 | $1/\epsilon = 1.32$ | 0.50 | 24.00 |
| 6 | 0.65 | 60 | $1/\epsilon = 1.54$ | 0.50 | 8.65 |
| 7 | 0.65 | 60 | $1.6/\epsilon = 2.46$ | 0.50 | 5.41 |
| 8 | 0.31 | 75 | $1/\epsilon = 3.23$ | 0.10 | 1.07 |
| 9 | 0.45 | 55 | $1/\epsilon = 2.22$ | 0.07 | 2.62 |

Fibres 1 and 2 (identical to fibres 8 and 9, respectively, of Table 1 ) are the commercially available hollow fibres from Microdyne Modulgebau. Fibre No. 3 is a hypothetical fibre of a membrane material of the same characteristics as membrane No. 1 (Goretex 2) of Table 1. Fibre No. 4 is a hypothetical fibre of the same characteristics as fibre No. 3, but with the average pore size increased to 0.5 $\mu$m. Fibre No. 5 is identical with Fibre No. 4, but with the thickness reduced to half. Fibres Nos. 6 and 7 are hypothetical fibres with identical characteristics, except for the tortuosity factor; Fibre No. 6 has the ideal geometric structure ($\tau=1/\epsilon$), while Fibre No. 7 falls outside the scope of the present invention ($\tau=1.6/\epsilon$). Fibres Nos. 8 and 9 are PTFE fibres disclosed in EP-A 0351584, with average pore size estimated from the given maximum pore diameter and the minimum value for tortuosity factor estimated as $1/\epsilon$. Fibre No. 8 has a hydraulic permeability for nitrogen, $N_2$, as reported in EP-A 0351584, of approximately twice that of Fibre No. 9, but as will be noted, the estimated (using Equation 3) membrane mass transfer coefficient for Fibre No. 9 is 2.6 times larger than that of Fibre No. 8, which clearly indicates the non-applicability of hydraulic permeability measurement for diffusion transport processes, as further discussed in comparative Example 2. Following the disclosure of the present invention this clearly illustrates how the technique disclosed in EP-A 0351584 can be suitably modified for producing the fibres having desired characteristics.

A comparison of the hypothetical mass transfer coefficient, $k_m$ for Fibre No. 6 with that of Fibre No. 7 shows that Fibre No. 6, having a tortuosity factor of $\tau=1/\epsilon$, shows a 50% increase in the membrane mass transfer coefficient compared to Fibre No. 7 which has a tortuosity factor of $\tau=1.6/\epsilon$, the increase, thus, being solely due to the difference in tortuosity factor. The data for Fibre No. 5 demonstrate how the wall morphology parameters can be combined in a suitable manner to provide a very high membrane mass transfer coefficient (about 10 times higher than any of the known fibres), provided the tortuosity factor is low.

As will appear from data given below, such very high mass transfer coefficient are extremely valuable from a economical point of view, both with respect to investment costs and with respect to operation costs.

To optimally utilize the advantages of these very highly efficient mass transfer membranes, suitable module designs will be important, such as will appear from the data given in Tables 3–6 below.

Tables 3–6 give data for module designs using a number of fibres all having an external diameter of 0.5 mm and having membrane mass transfer coefficients similar to those given in Table 2, with unspecified wall morphology. The modules are constructed from woven hollow fibre mats with different packing densities (0.6 and 0.1, respectively). Tables 3 and 4 give the estimated membrane area, number of fibre layers, pressure drop of gas for 95% $SO_2$ removal from 1 m$^3$ (293.15K)/s gas containing 1500 ppmv $SO_2$ at a constant superficial gas velocity of 1 m/s (based on a module cross-sectional area for gas flow of 1 m$^2$), perpendicular to the hollow fibres, using a high capacity absorbent, such as a 0.5 molar aqueous sodium sulfite solution, assuming to provide a negligible liquid side mass transfer resistance under all circumstances considered. The tables also give the ratios $k_m/k_g$ (the membrane mass transfer coefficient with respect to the mass transfer in question relative to the mass transfer film coefficient, with respect to the mass transfer in question, of the fluid ($SO_2$) having the lower transfer film coefficient with respect to the mass transfer in question).

As appears from the tables, the area required, the number of fibre layers and the gas side pressure drop all decrease with increasing membrane mass transfer coefficient, thus resulting in a much more efficient process when utilizing the principles of the present invention. It is also seen from the results in Tables 3 and 4 that by decreasing the packing density of the module, the total membrane area required is increased, however, the gas side pressure drop encountered is reduced markedly.

TABLE 3

Constant superficial gas velocity of 1 m/s and packing fraction = 0.6.

| Fiber no. | $A_{tot}$, m² | No. of layers | $\Delta P_{gas}$, Pa | $k_m/k_g$ | $k_o/k_m$ |
|---|---|---|---|---|---|
| 1 | 223.8 | 93.2 | 1092 | 0.103 | 0.904 |
| 2 | 405.4 | 168.9 | 1979 | 0.054 | 0.947 |
| 3 | 49.9 | 20.8 | 243 | 0.730 | 0.571 |
| 4 | 45.6 | 19.0 | 222 | 0.859 | 0.531 |
| 5 | 33.9 | 14.1 | 165 | 1.667 | 0.368 |
| 6 | 56.0 | 23.3 | 273 | 0.601 | 0.612 |
| 7 | 76.8 | 32.0 | 375 | 0.375 | 0.721 |
| 8 | 301.4 | 125.6 | 1471 | 0.076 | 0.928 |
| 9 | 135.7 | 56.5 | 662 | 0.182 | 0.842 |

TABLE 4

Constant superficial gas velocity of 1 m/s and packing fraction = 0.1.

| Fiber no. | $A_{tot}$, m² | No. of layers | $\Delta P_{gas}$, Pa | $k_m/k_g$ | $k_o/k_m$ |
|---|---|---|---|---|---|
| 1 | 242.8 | 606.9 | 58 | 0.196 | 0.834 |
| 2 | 424.4 | 1061 | 102 | 0.103 | 0.905 |
| 3 | 68.8 | 172.1 | 17 | 1.395 | 0.413 |
| 4 | 64.5 | 161.3 | 16 | 1.644 | 0.375 |
| 5 | 52.8 | 132.1 | 13 | 3.18 | 0.236 |
| 6 | 75.0 | 187.5 | 18 | 1.148 | 0.462 |
| 7 | 95.7 | 239.3 | 23 | 0.712 | 0.578 |
| 8 | 320.3 | 801.0 | 77 | 0.142 | 0.874 |
| 9 | 154.7 | 386.7 | 37 | 0.347 | 0.739 |

Tables 5 and 6 show data for alternate module designs, based on hypothetical fibres listed in Table 2, for a constant gas side pressure drop of 500 Pa by varying the gas flow rate for a module cross-sectional area of 1 m², using a high capacity absorbent such that the liquid side mass transfer resistance is negligible under all circumstances considered. A higher membrane mass transfer coefficient allows operation at higher superficial velocities, and/or a lower membrane area. Table 5 and Table 6 indicates that considerable savings in membrane area can be achieved by utilizing highly efficient mass transfer membranes. Further the high superficial gas velocities in table 6, show that such mass transfer apparatus can be operated at higher gas velocities than possible in any known mass transfer apparatus provided the membrane mass transfer coefficient is high enough and the liquid side mass transfer resistance remains negligible.

TABLE 5

Constant gas pressure drop of 500 Pa and packing fraction 0.6.

| Fiber no. | $\Delta P_{gas}$, Pa | $V_{sup}$, m³/(m²s) | $A_{tot}$, m² | No. of layers | $k_m/k_g$ | $k_o/k_m$ |
|---|---|---|---|---|---|---|
| 1 | 500 | 0.55 | 236.5 | 98.6 | 0.166 | 0.855 |
| 2 | 500 | 0.34 | 433.7 | 180.7 | 0.128 | 0.886 |
| 3 | 500 | 1.78 | 42.2 | 17.6 | 0.460 | 0.675 |
| 4 | 500 | 1.92 | 37.1 | 15.5 | 0.509 | 0.652 |
| 5 | 500 | 2.57 | 22.8 | 9.5 | 0.780 | 0.546 |
| 6 | 500 | 1.61 | 49.4 | 20.6 | 0.410 | 0.701 |
| 7 | 500 | 1.25 | 73.4 | 30.6 | 0.315 | 0.755 |
| 8 | 500 | 0.44 | 320.6 | 133.6 | 0.143 | 0.873 |
| 9 | 500 | 0.81 | 139.5 | 58.1 | 0.215 | 0.711 |

TABLE 6

Constant gas pressure drop of 500 Pa and packing fraction 0.1.

| Fiber no. | $\Delta P_{gas}$ Pa | $V_{sup}$ m³/(m²s) | $A_{tot}$ m² | No. of layers | $k_m/k_g$ | $k_o/k_m$ |
|---|---|---|---|---|---|---|
| 1 | 500 | 2.38 | 404.5 | 1011.3 | 0.052 | 0.949 |
| 2 | 500 | 3.27 | 218.4 | 546.0 | 0.0761 | 0.927 |
| 3 | 500 | 8.14 | 36.5 | 91.3 | 0.261 | 0.780 |
| 4 | 500 | 8.73 | 31.8 | 79.5 | 0.290 | 0.760 |
| 5 | 500 | 11.39 | 18.8 | 46.9 | 0.455 | 0.665 |
| 6 | 500 | 7.47 | 43.2 | 108.0 | 0.230 | 0.802 |
| 7 | 500 | 6.05 | 65.4 | 163.5 | 0.170 | 0.847 |
| 8 | 500 | 2.79 | 298.1 | 745.2 | 0.0625 | 0.939 |
| 9 | 500 | 4.31 | 127.3 | 318.2 | 0.108 | 0.898 |

Comparative Example 2
Comparison of Characterization by Permeability and Diffusivity Measurements Hydraulic permeability measurements and diffusivity measurements may give very different results, when used for characterising suitable membranes for diffusive processes.

For instance a microporous membrane with an 0.2 μm average pore size may have a hydraulic permeability $P_1$ measured by a hydraulic permeability measurement and a diffusivity of $D_{comb1}$ measured by a diffusivity measurement. Doubling the average pore size to 0.4 μm while keeping the porosity the same, will increase the permeability by four times (about 400%), but the diffusive flux for $SO_2$ will only be increased by about 15%.

The difference arise because the pore size and a distribution of pore sizes affects viscous and diffusive flow differently.

The total viscous flux is proportional to $r_p^2$. Therefore the total viscous flux will be dominated by contributions from the largest pores.

The diffusive flux, on the other hand, is proportional to $r_p$ to a power between 0 and 1 as described by equation 4–5 herein. For a wide range of relevant pore sizes for use in a method according to the present invention, the dependency of the pore size will be closer to 0 than 1.

Hence, permeability measurements may not be suitable for characterizing the microporous membranes for use in processes, where the major transport occurs by diffusion.

EXAMPLE 1
$SO_2$ Absorption into Aqueous Sodium Sulfite Solution (Membrane+Module)

The membrane and module according to the present invention are very well suited for transfer of $SO_2$ from a combustion flue gas into a sodium sulfite solution. As an example of a module in industrial scale for high mass transfer rate processes requiring short gas residence time, the module shown in FIG. 7 is referred to.

Figure 22:
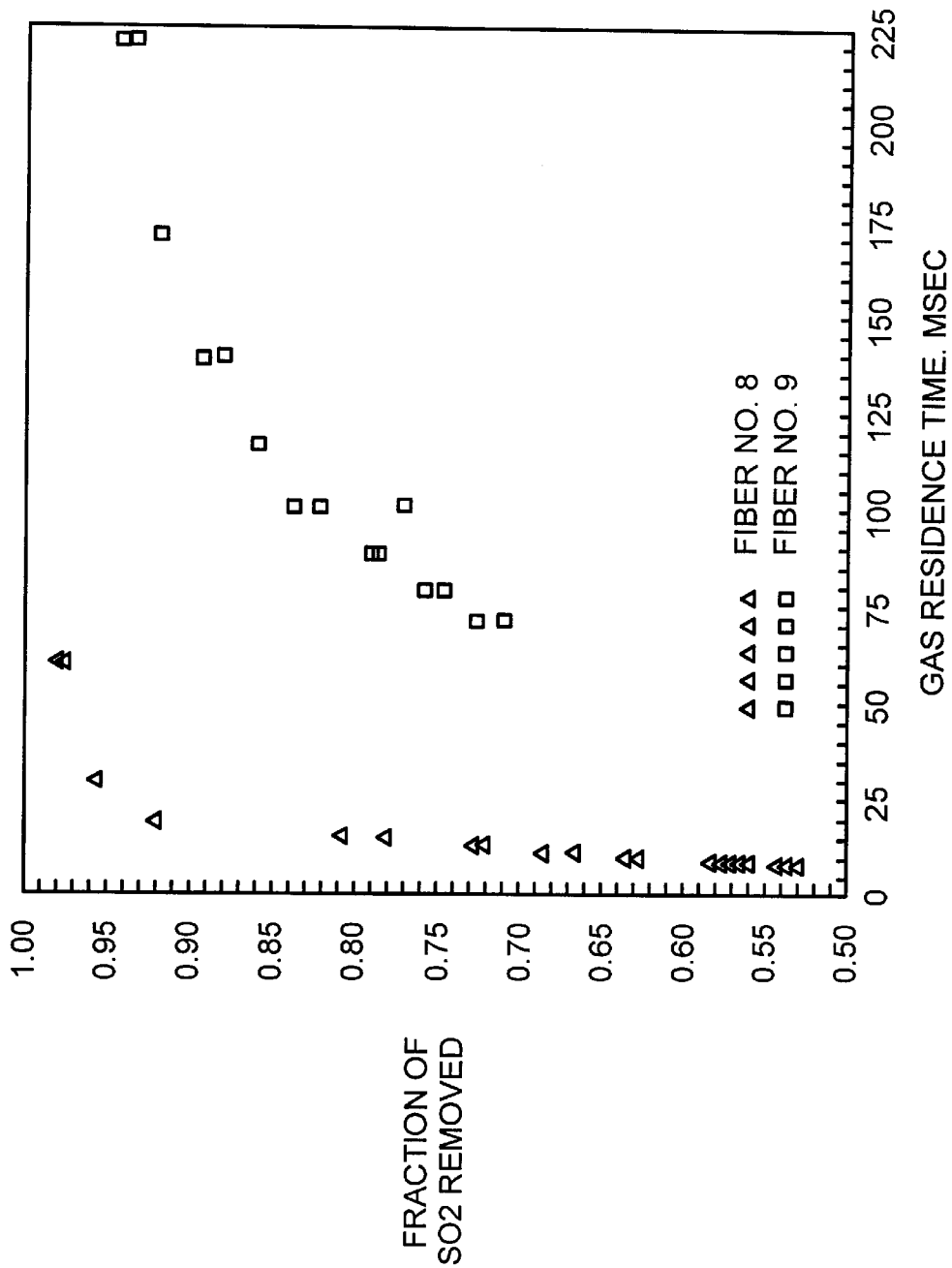
FIG. 22 illustrates experimental results of the fraction of $SO_2$ removed as a function of gas residence time for two hollow fibres.

The requirement of gas residence time for $SO_2$ removal has been studied in our laboratory. FIG. 22 shows the $SO_2$ removal versus gas residence time for 2 fibres (fibres No. 8 and 9 in Table 1). As seen from the figure only a very short gas—liquid contacting time is required for a high $SO_2$ removal efficiency. This gas—liquid contacting time can be further reduced if the membrane mass transfer coefficient can be increased, as shown in our laboratory for other membranes. Therefore, an efficient module for this application should provide a short gas residence time. This is obtained in the proposed invention for membrane module.

EXAMPLE 2
Stripping of Water from Thermosensitive Compounds (Membrane and Module)

Water can be stripped from a solution containing thermosensitive compounds into a gas phase at temperatures below the boiling point of the solution. Thereby thermosensitive compounds such as fruit juices, aroma compounds, enzymes, proteins, lipids, saccharides, pharmaceuticals, polymers, etc. can be concentrated without thermal degradation.

For efficient operation of the contacting apparatus the temperature should generally be as high as the solution allows, such as 25–75° C.

An inert stripping gas such as $N_2$, Ar, He, $CO_2$ is often preferred to avoid chemical degradation.

An efficient mass transfer apparatus for such applications is provided by use of a membrane specified according to the invention. However, most known module designs cannot provide a sufficiently small gas residence time to avoid saturation of the gas phase. Hence, the efficiency of such a mass transfer apparatus are often limited by the module design as illustrated by FIGS. 23 and 24.

Figure 23:
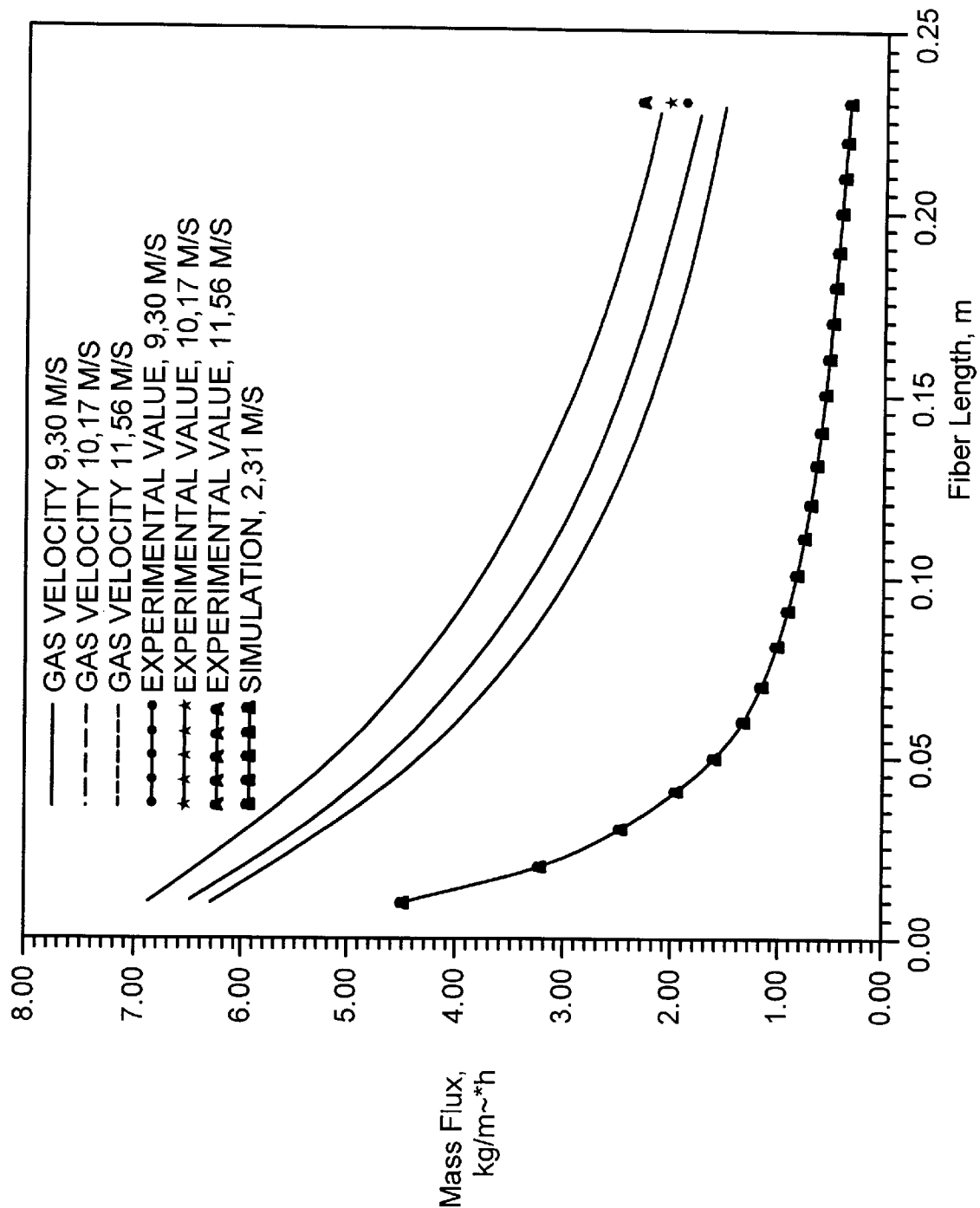
FIG. 23 illustrates experimental and simulated results of the mass flux of water as a function of fibre length and gas velocity.
Figure 24:
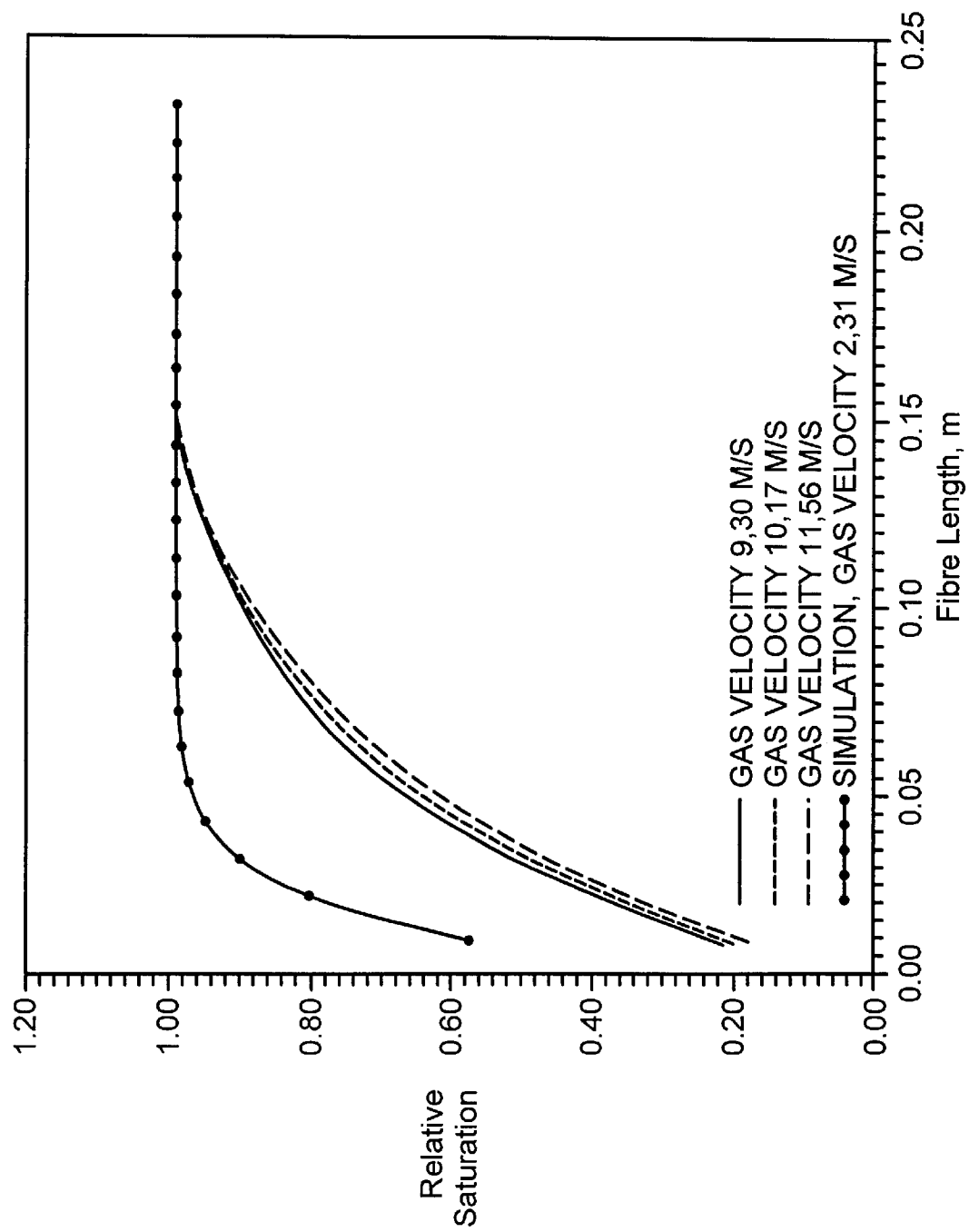
FIG. 24 illustrates simulated results of the relative saturation of the gas phase as a function of fibre length and gas velocity.
Figure 25:
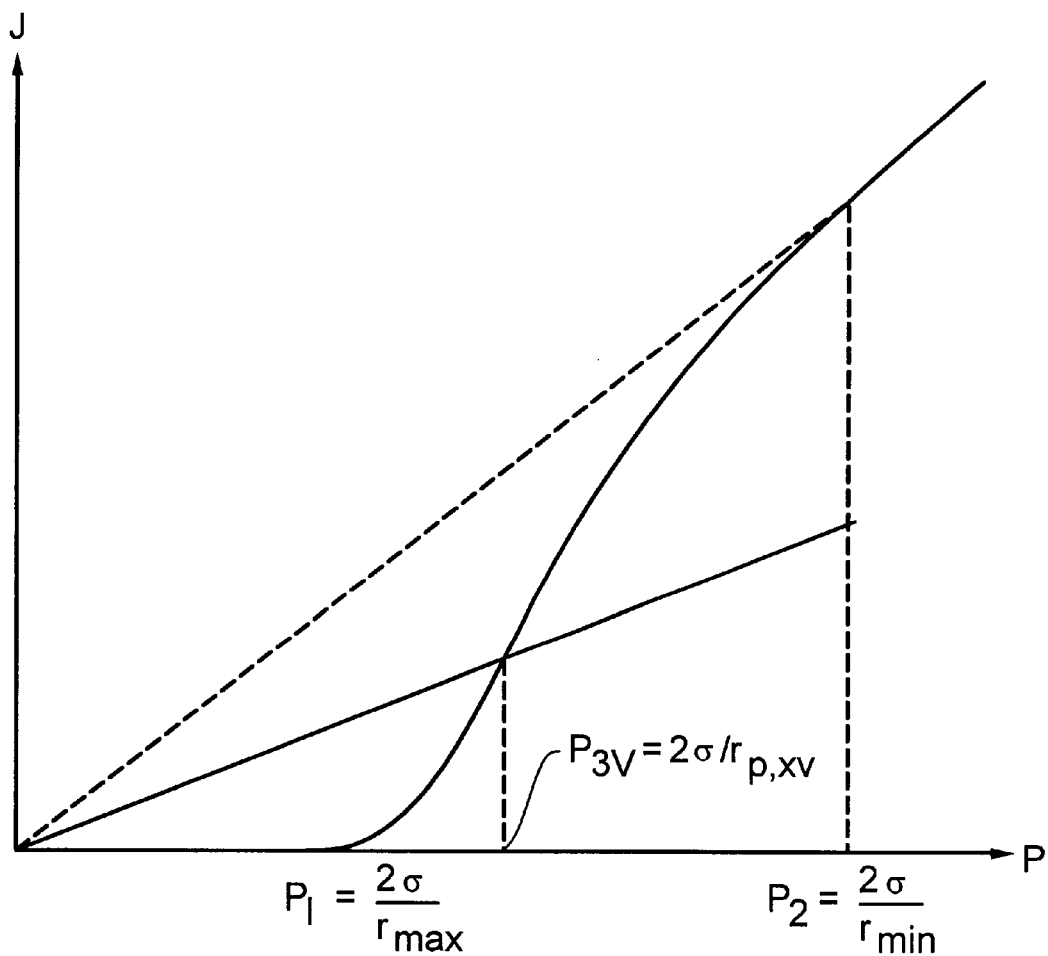
FIG. 25. Determination of the average pore size by the bubblepoint method.

FIG. 23 shows simulated and experimental results for the mass flux of water as a function of the module length and air velocity. Air was fed to the lumens of commercial hollow fibres, made from polypropylene, at a temperature of 26.5° C. and a pure water was fed to the shell side in a concurrent flow at a temperature of 40.6° C. The water flow was kept sufficiently high to avoid any polarisation phenomena to occur on the shell side. The effective fibre length was 23 cm. The mass flux of water was measured by condensing it in a condensing unit external to the module and measuring the weight of the condensate.

As illustrated in FIG. 23, the mass flux shows a steep decline within a short fibre length. At gas velocities as high as 10 m/s, the mass flux is reduced to half within the first 10 cm. At lower gas velocities, the module length for 50% mass flux reduction is only a few centimetres. The mass flux reduction is caused by a reduction in the driving force for mass transfer (a partial pressure difference), due to saturation of the gas phase as illustrated in FIG. 24. Hence, an efficient module for this application should allow a short gas residence time and a large gas velocity. This is provided by the apparatus according to the invention.

What is claimed is:

1. A method for transferring mass between a flow of a first fluid and a flow of a second fluid, one of the fluids being a gas phase and the other being a liquid phase, comprising contacting the first fluid with the outer surface of at least one porous membrane in the form of at least one hollow fibre of a poly(halogenated olefins), the pores of which membranes are gas-containing and have an average pore size between 0.2 and 1 $\mu$m, and contacting the second fluid with the inner surface of said membranes, the maximum pore size of said membranes being such as to prevent direct mixing of the two fluids, the membranes having a porosity ($\epsilon$) of at least 0.50 and at most 0.90, the tortuosity factor of the membranes being at the most $1.4/\epsilon$ when the porosity $\epsilon$ is lower than 0.80 and at the most $1.3/\epsilon$ when the porosity $\epsilon$ is 0.80 or higher, the liquid phase resistance with respect to the mass being transferred in the liquid ($1/k_{i,l}$) being substantially negligible and the mass transfer coefficient of the membranes with respect to the mass being transferred in the liquid ($1/k_{i,l}$) being at least 3 cm/s, wherein the thickness of the membrane is in the range of 5–200 $\mu$m.

2. A method according to claim 1, wherein the external diameter of the hollow membranes is in the range of 0.2–1.5 mm.

3. A method according to claim 2, wherein the ratio between the external diameter and the membrane thickness of the fibre is in the range of 5–15.

4. A method according to claim 3, wherein the porosity of the membranes is in the range of 0.60–0.90.

5. A method according to claim 1, wherein the external diameter of the fibre is in the range of 0.3–0.7 mm, the membrane thickness is 20–50 $\mu$m, the average pore size of the membranes is in the range of 0.2–0.6 $\mu$m, the porosity of the membranes is at least 0.70, and the tortuosity factor of the membranes is in the range $1/\epsilon$–$1.3/\epsilon$.

6. A method for transferring mass between a flow of a first fluid and a flow of a second fluid, one of the fluids being a gas phase and the other being a liquid phase, the method comprising contacting the first fluid with the outer surface of a plurality of hollow tubular members, at least a part of the walls of the hollow tubular members comprising porous membranes of poly(halogenated olefins) with gas-containing pores that have an average pore size between 0.1 and 1.5 $\mu$m, and contacting the second fluid with the inner surface of said hollow tubular members; the hollow tubular members being arranged parallel to each other or at angles to each other thereby defining an array of hollow tubular members, the plurality of hollow tubular members further defining interstices therebetween through which interstices the first fluid is moved in a transverse direction relative to the longitudinal direction of the hollow tubular members; the mass transfer coefficient of the membrane (Ki,m) with respect to said mass being at least 1 cm/s and further being at least one tenth of the mass transfer coefficient of the gas phase (Ki,g) with respect to said mass; the packing fraction of the array of hollow tubular members being in the range of 0.2 to 0.8; the pressure drop over the array of hollow tubular members being at the most 4000 Pa; and, wherein the membrane area per cubic meter of gas phase handled per second ($A_m/G$) for $C_1/C_2$ is equal to or greater than 20 and is defined by $$A_m/G = \ln((C_1 - C^*_1)/(C_2 - C^*_2))/K_0$$

wherein $K_0$ is the overall mass transfer coefficient, $C_1$ being the inlet concentration, in the gas, of the component in question, is at most 200 $m^2/(m^3/s)$ where each of the equilibrium concentrations of the gas component in question over the liquid phase $C^*_1$ and $C^*_2$ is at most $0.05C$, and wherein the thickness of the membrane is in the range of 5–200 $\mu$m.

7. A method according to claim 6, wherein the first fluid is a gas and the second fluid is a liquid.

8. A method according to claim 6, wherein substantially all of the walls of the hollow tubular members comprise porous membranes with gas-containing pores.

9. A method according to claim 6, wherein the membranes have a porosity ($\epsilon$) of at least 0.50 and at most 0.90, and the tortuosity factor of the membranes is at the most $1.4/\epsilon$ when the porosity $\epsilon$ is lower than 0.80 and at the most $1.3/\epsilon$ when the porosity $\epsilon$ is 0.80 or higher.

10. A method according to claim 6, wherein the porosity of the membranes is in the range of 0.75–0.90.

11. A method according to claim 6, where in the tortuosity factor of the membranes is at the most $1.3/\epsilon$.

12. A method according to claim 6, wherein the hollow tubular members are hollow fibres.

13. A method according to claim 6, wherein the hollow tubular members are elongated chambers arranged longitudinally substantially parallel to each other, the longitudinal surfaces of the chambers having at least one region being constituted by at least one porous membrane having gas-containing pores.

14. A method according to claim 13, wherein the chambers is/are supported by a supplementary structure.

15. A process where a mass is transferred between a flow of a first fluid and a flow of a second fluid, one of the fluids being a gas phase and the other phase being a liquid phase, the first fluid being contacted with the outer surface of a plurality of porous membranes made of a poly(halogenated olefin) in the form of hollow fibres with gas-containing pores that have an average pore size between 0.1 and 1.5 $\mu$m and the second fluid being contacted with the inner surface of said membranes, the process being an absorption or a desorption process in which a component is removed from a gas or liquid phase, respectively, wherein the membrane area per cubic meter of gas phase handled per second ($A_m/G$), for $C_1/C_2$ equal to or greater than 20 and is defined by $$A_m/G = \ln((C^*_1 - C_1)/(C_2 - C^*_2))/K_0$$

wherein $K_0$ is the overall mass transfer coefficient, $C_1$ being the inlet concentration, in the gas, of the component in question, is at most 200 m$^2$/(m$^3$/s) where each $C^*$ is at most 0.05C, or is at most 200 m$^2$/(m$^3$/s) where each $C^*$ is greater than 0.05 C, wherein the thickness of the membrane is in the range of 5–200 $\mu$m.

* * * * *